United States Patent [19]

Clark

[11] Patent Number: 4,791,108
[45] Date of Patent: Dec. 13, 1988

[54] SULFONYL-DECAHYDRO-8H-ISOQUINO[2,1-G][1,6]-NAPHTHYRIDINES AND RELATED COMPOUNDS USEFUL AS $\alpha_2$-BLOCKERS

[75] Inventor: Robin D. Clark, Palo Alto, Calif.

[73] Assignee: Syntex (U.S.A.) Inc., Palo Alto, Calif.

[21] Appl. No.: 37,320

[22] Filed: Apr. 13, 1987

[51] Int. Cl.[4] .................... A61K 31/47; C07D 455/03
[52] U.S. Cl. ................... 514/233.2; 514/255; 514/280; 514/285; 544/125; 544/361; 546/48; 546/70
[58] Field of Search .............. 546/48, 70; 544/125, 544/361; 514/280, 285, 229, 255, 233.2

[56] References Cited

U.S. PATENT DOCUMENTS

| | | | |
|---|---|---|---|
| 3,953,598 | 4/1976 | Hall ..................... | 514/280 |
| 4,076,820 | 2/1978 | Archibald et al. ............. | 546/95 X |
| 4,353,911 | 10/1982 | Buzas ..................... | 546/70 X |
| 4,454,114 | 6/1986 | Ward et al. ................ | 546/95 X |
| 4,550,114 | 10/1985 | White ..................... | 514/294 |
| 4,673,680 | 6/1987 | Pendleton ................. | 514/285 |
| 4,690,928 | 9/1987 | Huff et al. ................ | 514/285 |

OTHER PUBLICATIONS

Investigation in the Chemistry of Berbans, by Lajor Szabo, et al, Nouv. J. Chim., 4(3), 199-202, (1980).

Primary Examiner—Donald G. Daus
Assistant Examiner—Diana G. Rivers
Attorney, Agent, or Firm—Brian Lewis; Ellen J. Wise; Tom M. Moran

[57] ABSTRACT

Compounds of formulas (1) and (2):

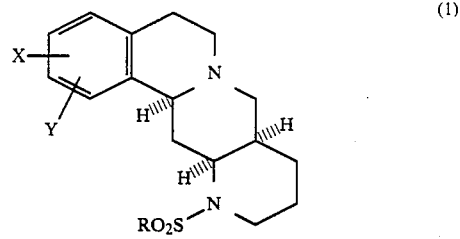

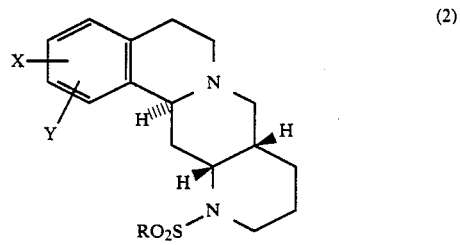

in which:
X and Y are independently hydrogen, hydroxy, lower alkyl, lower alkoxy or halo, or X and Y taken together is methylenendioxy or ethylene-1,2-dioxy, and
R is lower alkyl, optionally substituted phenyl, —$(CH_2)_mOR^1$ or —$NR^1R^2$, wherein m is an integer of 1 to 6 and $R^1$ and $R^2$ are independently hydrogen or lower alkyl, or —$NR^1R^2$ taken together is a heterocycle of the formula:

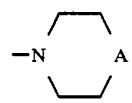

wherein A is —$CH_2$—, —$NR^1$— or oxygen,
or a pharmaceutically acceptable salt thereof, are useful as $\alpha_2$-blockers, especially as antidepressants.

28 Claims, No Drawings

SULFONYL-DECAHYDRO-8H-ISOQUINO[2,1-G][1,6]-NAPHTHYRIDINES AND RELATED COMPOUNDS USEFUL AS α₂-BLOCKERS

BACKGROUND OF THE INVENTION

1. Field of the Invention

The invention relates to various sulfonyldecahydro-8H-isoquino[2,1-g][1,6]naphthyridines which exhibit $\alpha_2$-blockade in mammals, and which, therefore, are useful as medicaments for the treatment of physiological conditions affected by such blockade. Such activities include, for example, amelioration of depression, inhibition of platelet aggregation, palliation of diabetes, alleviation of male impotence, weight-loss stimulation and lowering of intraoccular pressure.

2. Previous Disclosures

The novel compounds of this invention are various sulfonyldecahydro-8H-isoquino[2,1-g][1,6]naphthyridines, useful as $\alpha_2$-blockers. Compounds somewhat structurally related are described in U.S. Pat. Nos. 3,953,598, 4,353,911, 4,454,139, 4,550,114, and in Nouveau J. Chim. 4(3), 199–202 (1980).

SUMMARY OF THE INVENTION

One aspect of the invention concerns novel compounds represented by the formulas:

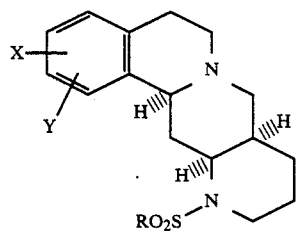

(1)

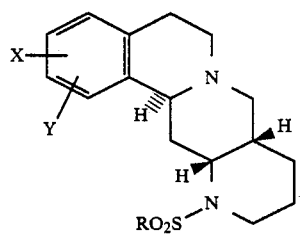

(2)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy, and R is lower alkyl of one to six carbon atoms, phenyl optionally substituted by one or two substituents chosen from halo or nitro groups or lower alkyl or lower alkoxy groups of one to four carbon atoms, —(CH₂)ₘOR¹ or —NR¹R² wherein m is an integer of 1 to 6 and R¹ and R² are independently hydrogen or lower alkyl, or —NR¹ R² taken together is a heterocycle of the formula:

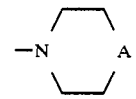

wherein A is —CH₂—, —NR¹— or oxygen;
or a pharmaceutically acceptable salt thereof.

Other aspects of the invention relate to the methods of preparation of compounds of formulas (1) and (2) thereof, to pharmaceutical compositions containing such compounds in admixture with one or more pharmaceutically acceptable, non-toxic carriers, and to methods pertaining to their use.

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like;

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated, for example phenyl optionally substituted by lower alkyl groups of one to four carbon atoms.

"Lower alkoxy" means the group -OR wherein R is lower alkyl as herein defined.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The term "(±)" is used to designate a racemic mixture of individual (+) and (−) isomers. The (±) racemate as well as the individual (+) and (−) enantiomers and non-racemic mixtures thereof are included within the scope of this invention.

The compounds of the invention will be named using the numbering system shown below.

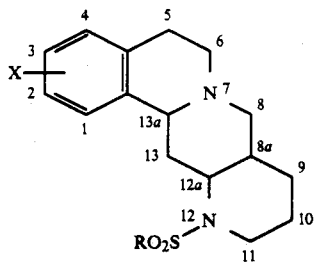

Following are examples of how representative compounds of formula (1) and (2) are named:

A compound of formula (1) wherein X is 3-methoxy, Y is hydrogen and R is methyl is named:

(±)-3-methoxy-12-methanesulfonyl-5,6,8aα,9,10,11,12,12aα,13,13aα-decahydro-8H-isoquino[2,1-g][1,6]naphthyridine.

A compound of formula (1) wherein X and Y are hydrogen and R is 2-methylpropyl is named:

(±)-12-(2-methylpropanesulfonyl)-5,6,8aα,9,10,11,12,12aα,13,13aα-decahydro-8H-isoquino[2,1-g][1,6]napthyridine.

A compound of formula (2) wherein X and Y taken together is 2,3-methylenedioxy and R is dimethylamino, is named:

(±)-2,3-methylenedioxy-12-(N,N-dimethylaminosulfonyl)-5,6,8aβ,9,10,11,12,12aβ,13,13aα-decahydro-8H-isoquino[2,1-g][1,6]naphthyridine.

Preferred Embodiments

Among the family of compounds of the present invention, a preferred group includes compounds of formula (1). Within this group a preferred subgroup includes the compounds in which X and Y are independently hydrogen or lower alkoxy, or X and Y taken together is methylenedioxy, and R is lower alkyl, —(CH$_2$)$_m$OR$^1$ or —NR$^1$R$^2$. One preferred class within this subgroup includes compounds in which X and Y taken together is methylenedioxy and R is methyl. A second preferred class within this subgroup includes compounds in which X is hydrogen or methoxy, Y is methoxy and R is methyl or 2-methoxyethyl, especially where X is hydrogen. A third preferred class within this subgroup includes compounds in which X and Y are hydrogen and R is methyl, 2-methoxyethyl or dimethylamino.

A second preferred group includes compounds of formula (2). Within this group a preferred subgroup includes the compounds in which X and Y are independently hydrogen or lower alkoxy, or X and Y taken together is methylenedioxy, and R is lower alkyl, —(CH$_2$)$_m$OR$^1$ or —NR$^1$R$^2$.

At present, the preferred compounds are:

(±)-3-methoxy-12-methanesulfonyl-5,6,8aα,9,10,11,12,12aα,13,13aα-decahydro-8H-isoquino[2,1-g][1,6]naphthyridine hydrochloride;

(±)-2,3-dimethoxy-12-methanesulfonyl-5,6,8aα,9,10,11,12,12aα,13,13aα-decahydro-8H-isoquino[2,1-g][1,6]naphthyridine hydrochloride;

(±)-12-methanesulfonyl-5,6,8aα,9,10,11,12,12aα,13,13aα-decahydro-8H-isoquino[2,1-g][1,6]naphthyridine hydrochloride;

(±)-12-(2-methoxyethanesulfonyl)-5,6,8aα,9,10,11,12,12aα,13,13aα-decahydro-8H-isoquino[2,1-g][1,6]naphthyridine hydrochloride;

(±)-3-methoxy-12-(2-methoxyethanesulfonyl)-5,6,8aα,9,10,11,-12,12aα,13,13aα-decahydro-8H-isoquino[2,1-g][1,6]naphthyridine hydrochloride; and (±)-12-(N,N-dimethylaminosulfonyl)-5,6,8aα,9,10,11,12,12aα,13,13aα-decahydro-8H-isoquino[2,1-g][1,6]naphthyridine hydrochloride.

Methods of Preparation

The compounds of formula (1) and (2) are prepared from the intermediates of formula (VII) and (VIII), the preparation of which is illustrated below in Reaction Scheme I.

It should be understood that the structures illustrated in Reaction Scheme I and in all subsequent Reaction Schemes are intended to represent racemic mixtures although, for the sake of clarity, only one enantiomer is shown.

REACTION SCHEME I

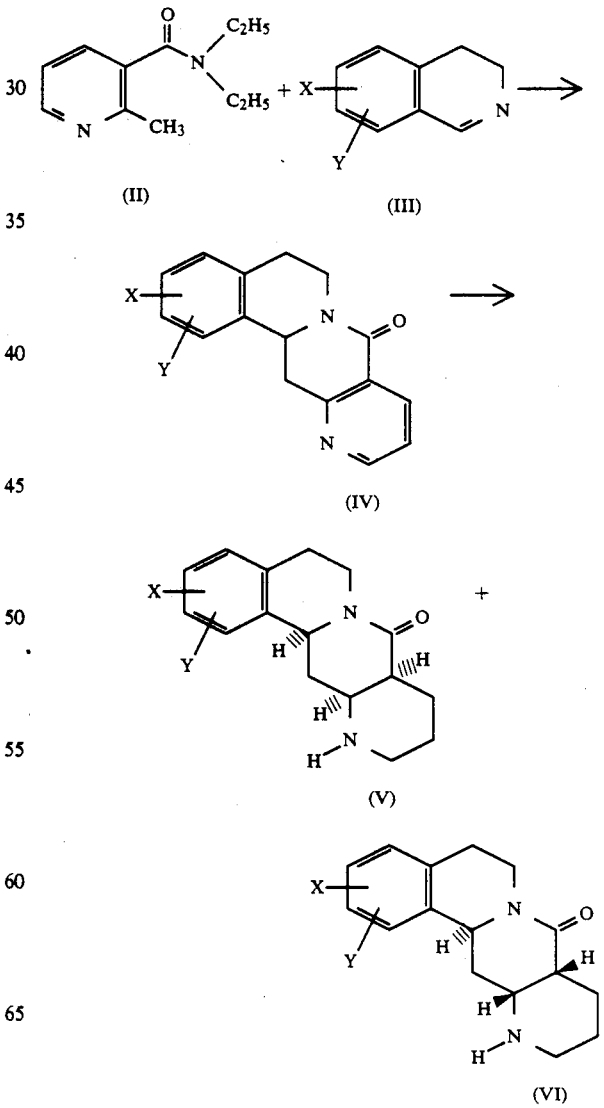

-continued
REACTION SCHEME I

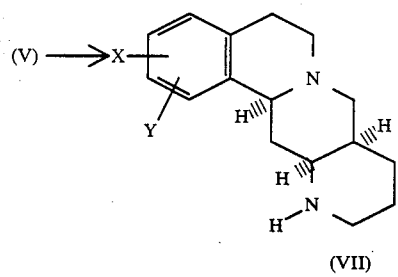

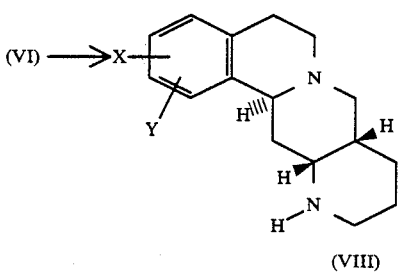

The intermediate of formula (II), 2-methylnicotinic acid diethylamide, is prepared according to the method disclosed in Ber., 72B, 563 (1939). The intermediates of formula (III), optionally substituted dihydroisoquinolines, are prepared according to the method of Bischler-Napieralski, disclosed in Organic Reactions, Vol. VI, p 74 (1951), by the cyclization of formamidines of commercially available optionally substituted phenylethylamines. To prepare the compounds of formula (IV), the compounds of formula (II) and (III) are reacted together in the presence of a strong base, for example potassium t-butoxide, sodamide, sodium triphenylmethane, lithium diethylamide or preferably lithium diisopropylamide. The reaction is preferably carried out in an ethereal solvent, for example diethyl ether, dimethoxyethane, dioxane or tetrahydrofuran, at a temperature of about 0° C. to −50° C., preferably at about −10° C. to −40° C., for about 30 minutes to 4 hours. For example, diisopropylamine is dissolved in an ethereal solvent, preferably tetrahydrofuran, and cooled to a temperature of about −20° to −80° C., preferably about −65° C. To the cooled solution about 1 molar equivalent of an alkyl lithium, preferably 1.6M n-butyllithium, is added. To this cold solution is added a mixture of about 1 molar equivalent of the compound of formula (II) and about 1 molar equivalent of the compound of formula (III) in an ethereal solvent, preferably tetrahydrofuran. The reaction mixture is allowed to warm to about −10° to −40° C., preferably about −20° C., over a period of about 1 hour, and the reaction then quenched with an acid, preferably hydrochloric acid. The product of formula (IV), a (±)-5,6,13,13a-tetrahydroisoquino[2,1-g][1,6]naphthyridine-8-one hydrochloride, is isolated and purified by conventional means, preferably recrystallization of an acid salt.

The compound of formula (IV) as an acid salt, preferably the hydrochloride, is then hydrogenated with a suitable heterogeneous catalyst, for example palladium on carbon, platinum oxide or preferably rhodium on alumina, to give a mixture of the diastereoisomers of formula (V) and (VI). For example, for every gram of the hydrochloride of the compound of formula (III) in a solution of acetic acid is added from 0.1 to 0.6 g, preferably about 0.25 g, of 5% rhodium on alumina catalyst and the mixture hydrogenated at a pressure of about 25–80 psi, preferably about 50 psi. The reaction is conducted at a temperature of about 0° to 50° C., preferably about 25° C., for about 24–72 hours, preferably about 42 hours. When the reaction is substantially complete, the mixture of compounds of formula (IV) and (V) is isolated by conventional means and the mixture chromatographed on silica gel, eluting with a suitable solvent mixture, for example 5–20% methanol in methylene chloride. The first component eluted is the compound of formula (V), followed by the compound of formula (VI).

The compounds of formula (V) and (VI) are then individually reduced to the compounds of formula (VII) and (VIII) with a suitable reducing agent, for example borane, triethyloxonium fluoroborate followed by sodium borohydride, sodium borohydride in the presence of a carboxylic acid, or preferably lithium aluminum hydride. For example, a solution of a compound of formula (V) in an ethereal solvent, preferably tetrahydrofuran, is slowly added to a solution of about 1 to 4 molar equivalents, preferably about 1.5 to 2 molar equivalents, of lithium aluminum hydride in the same ethereal solvent at about 25° C. The mixture is then refluxed for about 1–10 hours, preferably about 3 hours. When the reaction is substantially complete, the compound of formula (VII) is separated and purified by conventional means, for example recrystallization of an acid salt. In a similar fashion, the compound of formula (VI) is reduced to the compound of formula (VIII), and likewise separated and purified.

In a similar fashion the compounds of formula (VII) and (VIII) are obtained as a mixture if the above reduction is carried out on a mixture of the compounds of formula (V) and (VI). Such a mixture is obtained if the step of chromatographic separation is omitted from the procedure above for the preparation of the compounds of formula (V) and (VI).

Compounds of Formula (1) and (2)

Compounds of formula (1) and (2) are prepared from the compounds of formula (VII) and (VIII) is depicted in Reaction Sequence II below.

REACTION SCHEME II

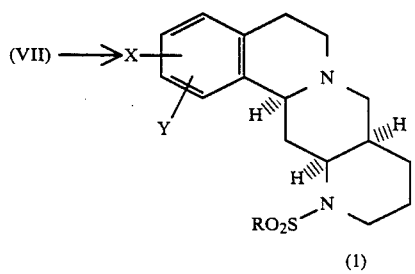

-continued
REACTION SCHEME II

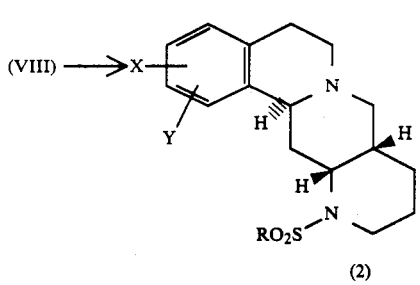

(2)

The compounds of formula (1) and (2) are prepared by reacting the corresponding individual compound of formula (VII) or (VIII) with a substituted sulfonyl halide of the formula $ZSO_2R$, where Z is chlorine or bromine and R is as defined above. The sulfonyl halides of formula $ZSO_2R$ are either commercially available from, inter alia, Aldrich Chemical Co., or may be prepared according to the method of Zeigler and Sprague, disclosed in J. Org. Chem., Vol 16, p 621 (1951).

For example, to prepare the compound of formula (1) the compound of formula (VII) is dissolved in an inert organic solvent, such as benzene, toluene, ethyl acetate, tetrahydrofuran, diethyl ether, chloroform or preferably dichloromethane, containing from 1–10 molar equivalents, preferably about 2 molar equivalents, of an inorganic base such as sodium carbonate, potassium bicarbonate or the like, or preferably a tertiary organic base, such as pyridine, N-methylpiperidine and the like, preferably triethylamine. The mixture is cooled to about $-10°$ to $10°$ C., preferably about $0°$ C., and about 1–4 molar equivalents, preferably about 1.25 molar equivalents, of the appropriately substituted sulfonyl halide of formula $ZSO_2R$ added and the mixture stirred for about 30 minutes to 4 hours, preferably about 1 hour at a temperature of about $10°$ to $40°$ C., preferably about $25°$ C. An inert solvent, preferably diethyl ether, is then added, and the compound of formula (1) separated and purified by conventional means, for example recrystallization of an acid salt. In a similar fashion, the compound of formula (2) is prepared from the compound of formula (VIII), the likewise separated and purified.

An alternative procedure for the preparation of compounds of formula (1) and (2) is from the mixture of compounds (VII) and (VIII) obtained as shown above in Reaction Scheme I. The mixture of compounds (VII) and (VIII) is treated with a substituted sulfonyl halide of formula $ZSO_2R$ in the same manner as shown above, giving a mixture of the compounds of formula (1) and (2) which is separated by conventional means, preferably chromatography, into the individual diastereoisomers of formula (1) and (2).

An alternative preparation of the compound of formula (1) is shown in Reaction Scheme III below.

REACTION SCHEME III

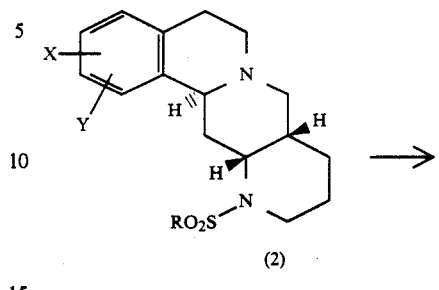

(2)

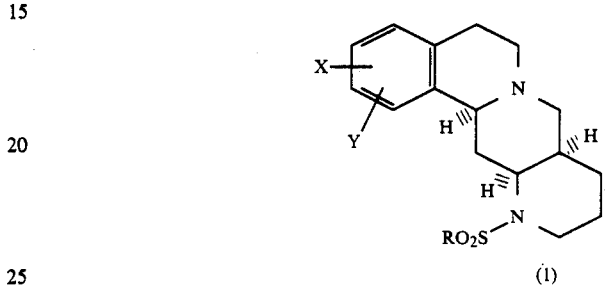

(1)

In this procedure, the compound of formula (2), prepared as shown in Reaction Scheme II, is converted to the compound of formula (1). Typically, the compound of formula (2) and about 1–10 molar equivalents, preferably about 4 molar equivalents, of a mercuric salt, preferably mercuric acetate, are combined in acetic acid containing from about 5%–50%, preferably about 10%, of water and the mixture heated at a temperature of about $70°$ C. to the reflux temperature, preferably about $105°$ C., for about 30 minutes to 4 hours, preferably about 1 hour. After filtering, hydrogen sulfide is passed through, followed by refiltering and removal of the solvent from the filtrate. The residue is then dissolved in a protic solvent, preferably ethanol, the solution cooled to a temperature of about $0°$ to $-40°$ C., preferably about $-20°$ C., and treated with about 1 to 10 molar equivalents, preferably about 4 molar equivalents, of sodium borohydride. When the reaction is substantially complete the compound of formula (1) is isolated by conventional means, for example chromatography.

A mixture of compounds of formula (1) and (2) may replace the compound of formula (2) as a starting material in the procedure described above, giving rise to the same product of formula (1). Such a mixture of compounds of formula (1) and (2) is obtained as shown in Reaction Scheme II.

The compounds of formula (1) and (2) in which R is $-(CH_2)_mOH$ are preferably prepared from the compounds of formula (1) and (2) in which R is $-(CH_2)_mOR^1$. Typically, the compound of formula (1) or (2) in which R is $-(CH_2)_mOR^1$ is dissolved in an inert solvent as defined above, preferably methylene chloride, and reacted with about 1 to 4 molar equivalents, preferably about 1.7 molar equivalents, of boron tribromide at a temperature of about $-40°$ C. to $-80°$ C., preferably about $-60°$ C. The mixture is then allowed to warm to about $0°$ C. to $40°$ C., preferably about $25°$ C. When the reaction is substantially complete the compound of formula (1) or (2) in which R is $-(CH_2)_mOH$ is isolated by conventional means, for example chromatography.

The compounds of formula (1) and (2) in which R is aminophenyl are preferably prepared from the corresponding compounds in which R is nitrophenyl; these are prepared by reacting the appropriate compounds of formula (VII) and (VIII) with a nitrobenzenesulfonyl chloride or bromide to give the corresponding compounds of the general formula (1) or (2) in which R is nitrophenyl, using the general method shown in Reaction Scheme I above. The latter compound is then dissolved in a protic solvent, preferably ethanol, and hydrogenated at about 50 psi in the presence of a palladium on carbon catalyst. When the reaction is substantially complete the compound of formula (1) or (2) in which R is aminophenyl is isolated by conventional means, for example crystallization of an acid salt.

Isolation and purification of the compounds and intermediates described herein can be effected, if desired, by an suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Examples hereinbelow. However, other equivalents separation or isolation procedures could, of course, also be used.

The salt products are also isolated by conventional means. For example, the reaction mixtures may be evaporated to a dryness, and the salts can be further purified by conventional methods such as those listed above.

The compounds of formula (1) and (2) have three or more asymmetric centers. Accordingly, they may be prepared in either optically active (+) or (−) form or as a (±) racemic mixture. Unless otherwise specified, the compounds described herein are all racemic mixtures. However, the scope of the invention described and claimed encompasses the individual optical isomers and non-racemic mixtures thereof as well as the racemic forms of the compounds of formula (1) and (2).

If desired, the compounds herein may be resolved into their optical antipodes by conventional resolution means; for example by separation (e.g. fractional crystallization) of the diastereomeric salts formed by the reaction of these compounds with optically active acids, at temperatures between 0° C. and the reflux temperature of the solvent employed for fractional crystallization. Exemplary of such optically active acids are the optically active forms of camphor-10-sulfonic acid, 2-bromo-camphor-10-sulfonic acid, camphoric acid, menthoxyacetic acid, tartaric acid, malic acid, diacetyl-tartaric acid, pyrrolidine-5-carboxylic acid and the like. The separated pure diastereomeric salts may then be cleaved by standard means, such as treatment with a base, to afford the respective optical isomers of the compounds of formula (1) or (2).

Salts of Compounds of Formula (1) and (2)

The compounds of formula (1) and (2) may be converted to a corresponding acid addition salt by virtue of the presence of the tertiary nitrogen atoms.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluene-sulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained at 0°–50° C. The resulting salt precipitates spontaneously or may be brought out of solution with a less polar solvent.

The acid addition salts of the compounds of formula (1) and (2) may be decomposed to the corresponding free bases by treatment with at least a stoichiometric amount of a suitable base such as sodium or potassium hydroxide, potassium carbonate, sodium bicarbonate, ammonia, and the like.

In summary, the compounds of the present invention are made by the procedures outlined below:

1. A process for preparing compounds of the formula (1) and (2) wherein:

X and Y are independently hydrogen, hydroxy, lower alkyl, lower alkoxy or halo, or X and Y taken together are methylenedioxy or ethylene-1,2-dioxy; and R is lower alkyl of one to six carbon atoms, phenyl optionally substituted by one or two substituents chosen from halo or nitro groups or lower alkyl or lower alkoxy groups of one to four carbon atoms, —(CH$_2$)$_m$OR$^1$ or —NR$^1$R$^2$ wherein m is an integer of 1 to 6 and R$^1$ and R$^2$ are independently hydrogen or lower alkyl, or —NR$^1$R$^2$ taken together is a heterocycle of the formula:

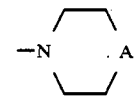

wherein A is —CH$_2$—, —NR$^1$— or oxygen; comprises:

(a) reacting a compound of the formula

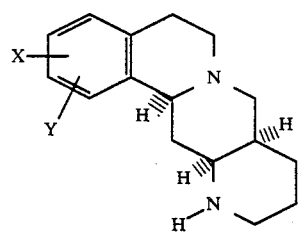

(VII)

or

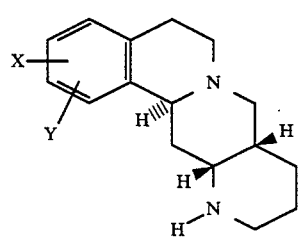

(VIII)

where X and Y are as defined above, with a substituted sulfonyl halide of the formula ZSO$_2$R, where Z is chlorine or bromine and R is as defined above, or (b) converting the free base of the compound of formula (1) or (2) with an acid to a pharmaceutically acceptable salt; or (c) converting an acid addition salt of the compound of formula (1) or (2) with a base to the corresponding free acid; or (d) converting an acid addition salt of the compound of formula (1) or (2) to another pharmaceutically acceptable acid addition salt.

2. Alternatively, a process for preparing compounds of formula (1) and (2), above, comprises:
reacting a mixture of compounds of the formula

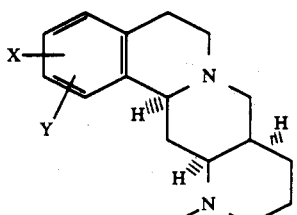
(VII)

and

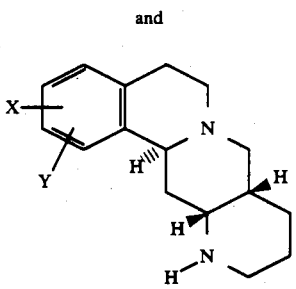
(VIII)

where X and Y are as defined above, with a substituted sulfonyl halide of the formula $ZSO_2R$, where Z is chlorine or bromine and R is as defined above, and separating the resultant mixture into the individual compounds of formula (1) and (2).

3. Alternatively, a process for preparing a compound of formula (1), above, comprises:
reacting a compound of the formula:

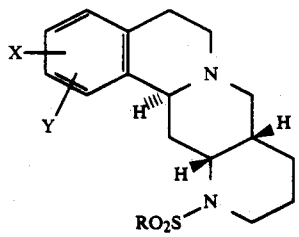
(2)

where X, Y and R are as defined above, with a mercuric salt followed by treatment with hydrogen sulfide and subsequent reduction with sodium borohydride.

Utility and Administration

The compounds of formula (1) and (2) and the pharmaceutically acceptable acid addition salts thereof have been found to possess valuable pharmacological properties in the central nervous system and, in particular, have been shown to block $\alpha_2$-receptors in standard laboratory tests. Accordingly these compounds and pharmaceutically acceptable compositions containing them are useful in the prevention, reduction and inhibition of depression in mammals, including humans, and in regulation of other physiological phenomena related to $\alpha_2$-receptors.

Other physiological activities include, for example, inhibition of platelet aggregation, palliation of diabetes, alleviation of male impotence, lowering of intraoccular pressure (useful in treating e.g. glaucoma) and stimulation of weight loss.

In applying the compounds of this invention to treatment of conditions which are regulated by the CNS, administration of the active compounds and salts described herein can be via any of the accepted modes of administration for agents which relieve depression or affect the central nervous system including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and an active compound of formula (1) or (2) or the pharmaceutically acceptable salts thereof and, in addition, may include other medicinal agents, pharmaceutical agents, carriers, adjuvants, etc.

The amount of active compound administered will of course, be dependent on the subject being treated, the severity of the affliction, the manner of administration and the judgment of the prescribing physician. However, an effective dosage is in the range of 0.01–1 mg/kg/day, preferably 0.1–0.5 mg/kg/day. For an average 70 kg human, this would amount to 0.7–70 mg per day, or preferably 7–35 mg/day.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

Dosage forms or compositions containing active ingredient (compounds of formula (1) and (2) or its salts)

in the range of 0.25 to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 5–50%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parental compositions is highly dependent on the specific nature thereof, as well as the activity of the compound and the needs of the subject. However, percentages of active ingredient of 0.1% to 10% in solution are employable, and will be higher if the composition is a solid which will be subsequently diluted to the above percentages. Preferably the composition will comprise 0.2–2% of the active agent in solution.

For systemic administration via suppository, traditional binders and carriers include, e.g. polyalkalene glycols or triglycerides. Such suppositories may be formed from mixtures containing active ingredient in the range of 0.5%–10%; preferably 1–2%.

In applying the compounds of the invention to treatment of diseases or disorders of the eye which are associated with an abnormally high intraoccular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.001% to 10%, most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical sterilants are phenyl mercuric acetate, thimerosal, chlorobutanol, and benzalconium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8–8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2–10 drops per day per eye of a 0.1% solution of active ingredient.

The following preparation and examples illustrate the invention but are not intended to limit its scope.

PREPARATION 1

Preparation of (±)-5,6,13,13a-Tetrahydroisoguino[2,1-g][1,6]naphthyridin-8-one hydrochloride and Related Compounds of Formula (IV).

A. Diisopropylamine (28 ml) and 150 ml of tetrahydrofuran were cooled to −65° C. and 125 mL of 1.6M n-butyllithium was added. To the resulting solution was added a solution of 16.2 g of 3,4-dihydroisoquinoline and 38.4 g of 2-methylnicotinic acid diethylamide in tetrahydrofuran. The mixture was allowed to warm to −20° C. and 600 ml of 3N hydrochloric acid was then added followed by 200 ml of water. The mixture was basified with $NH_4OH$ and extracted twice with ether. The ether extracts were combined, dried over anhydrous magnesium sulfate and evaporated to a residue, which was dissolved in methanol and acidified with anhydrous HCl in ether. Acetone (50 ml) was added and the mixture was allowed to stand overnight. The crystalline product was collected by filtration, yielding 34 g of (±)-5,6,13,13a-tetrahydroisoquino[2,1-g][1,6]naphthyridine-8-one hydrochloride, m.p. 220°–222° C.

An additional 7.5 g of the title compound as the free base was obtained by evaporation of the mother liquor followed by partitioning between ether and aqueous $NH_4OH$ and silica gel chromatography of the residue obtained from evaporation of the ether, eluting with ethyl acetate, giving the free base, m.p. 72°–73° C.

B. Similarly, replacing 3,4-dihydroisoquinoline with the appropriate compound of formula (III) and following the procedure in paragraph A above, the following compounds of formula (IV) were prepared:

(±)-3-methoxy-5,6,13,13a-tetrahydroisoquino[2,1-g][1,6]naphthyridine-8-one hydrochloride, m.p. 244°–246° C.;

(±)-3-methoxy-5,6,13,13a-tetrahydroisoquino[2,1-g][1,6]naphthyridine-8-one, m.p. 115°–116° C.;

(±)-2,3-dimethoxy-5,6,13,13a-tetrahydroisoquino[2,1-g][1,6]naphthyridine-8-one hydrochloride, m.p. 238°–240° C.;

(±)-1,4-dimethoxy-5,6,13,13a-tetrahydroisoquino[2,1-g][1,6]naphthyridine-8-one hydrochloride;

(±)-2,3-methylenedioxy-5,6,13,13a-tetrahydroisoquino[2,1-g][1,6]naphthyridine-8-one, m.p. 177°–179° C.; and (±)-2,3-(ethylene-1,2-dioxy)-5,6,13,13a-tetrahydroisoquino[2,1-g][1,6]naphthyridine-8-one.

C. Similarly, replacing 3,4-dihydroisoquinoline with other compounds of formula (III) and following the procedure in paragraph A above, the following exemplary compounds of formula (IV) are prepared:

(±)-1-methyl-5,6,13,13a-tetrahydroisoquino[2,1-g][1,6]naphthyridine-8-one hydrochloride;
(±)-2-methyl-5,6,13,13a-tetrahydroisoquino[2,1-g][1,6]naphthyridine-8-one hydrochloride;
(±)-3-methyl-5,6,13,13a-tetrahydroisoquino[2,1-g][1,6]naphthyridine-8-one hydrochloride;
(±)-2,3-dimethyl-5,6,13,13a-tetrahydroisoquino[2,1-g][1,6]naphthyridine-8-one hydrochloride;
(±)-3-ethyl-5,6,13,13a-tetrahydroisoquino[2,1-g][1,6]naphthyridine-8-one hydrochloride;
(±)-3-isobutyl-5,6,13,13a-tetrahydroisoquino[2,1-g][1,6]naphthyridine-8-one hydrochloride;
(±)-3-n-hexyl-5,6,13,13a-tetrahydroisoquino[2,1-g][1,6]naphthyridine-8-one hydrochloride;
(±)-1-methoxy-5,6,13,13a-tetrahydroisoquino[2,1-g][1,6]naphthyridine-8-one hydrochloride;
(±)-2-methoxy-5,6,13,13a-tetrahydroisoquino[2,1-g][1,6]naphthyridine-8-one hydrochloride;
(±)-4-methoxy-5,6,13,13a-tetrahydroisoquino[2,1-g][1,6]naphthyridine-8-one hydrochloride;
(±)-3-ethoxy-5,6,13,13a-tetrahydroisoquino[2,1-g][1,6]naphthyridine-8-one hydrochloride;
(±)-3-isobutoxy-5,6,13,13a-tetrahydroisoquino[2,1-g][1,6]naphthyridine-8-one hydrochloride;
(±)-3-n-hexyloxy-5,6,13,13a-tetrahydroisoquino[2,1-g][1,6]naphthyridine-8-one hydrochloride;
(±)-3-hydroxy-5,6,13,13a-tetrahydroisoquino[2,1-g][1,6]naphthyridine-8-one hydrochloride;
(±)-2,3-dihydroxy-5,6,13,13a-tetrahydroisoquino[2,1-g][1,6]naphthyridine-8-one hydrochloride;
(±)-1,2-dimethoxy-5,6,13,13a-tetrahydroisoquino[2,1-g][1,6]naphthyridine-8-one hydrochloride;
(±)-1,4-dimethoxy-5,6,13,13a-tetrahydroisoquino[2,1-g][1,6]naphthyridine-8-one hydrochloride;
(±)-3,4-dimethoxy-5,6,13,13a-tetrahydroisoquino[2,1-g][1,6]naphthyridine-8-one hydrochloride;
(±)-2,3-diethoxy-5,6,13,13a-tetrahydroisoquino[2,1-g][1,6]naphthyridine-8-one hydrochloride;
(±)-2,3-di-n-butoxy-5,6,13,13a-tetrahydroisoquino[2,1-g][1,6]naphthyridine-8-one hydrochloride;
(±)-1,2-methylenedioxy-5,6,13,13a-tetrahydroisoquino[2,1-g][1,6]naphthyridine-8-one hydrochloride;
(±)-3,4-methylenedioxy-5,6,13,13a-tetrahydroisoquino[2,1-g][1,6]naphthyridine-8-one hydrochloride;
(±)-1-chloro-5,6,13,13a-tetrahydroisoquino[2,1-g][1,6]naphthyridine-8-one hydrochloride;
(±)-2-chloro-5,6,13,13a-tetrahydroisoquino[2,1-g][1,6]naphthyridine-8-one hydrochloride;
(±)-3-chloro-5,6,13,13a-tetrahydroisoquino[2,1-g][1,6]naphthyridine-8-one hydrochloride;
(±)-4-chloro-5,6,13,13a-tetrahydroisoquino[2,1-g][1,6]naphthyridine-8-one hydrochloride;
(±)-3-bromo-5,6,13,13a-tetrahydroisoquino[2,1-g][1,6]naphthyridine-8-one hydrochloride;
(±)-3-fluoro-5,6,13,13a-tetrahydroisoquino[2,1-g][1,6]naphthyridine-8-one hydrochloride; and
(±)-2-fluoro-5,6,13,13a-tetrahydroisoquino[2,1-g][1,6]naphthyridine-8-one hydrochloride.

PREPARATION 2

Preparation of (±)-5,6,8aα,9,10,11,12,12aα,13,13aα-decahydroisoquino[2,1-g][1,6]naphthyridin-8-one (V) and (±)-5,6,8aβ,9,10,11,12,12aβ,13,13aα-Decahydroisoquino[2,1-g][1,6]naphthyridin-8-one (VI) and Related Compounds of Formula (V) and (VI)

A. A mixture of 30 g of (±)-5,6,13,13a-tetrahydroisoquino[2,1-g][1,6]naphthyridine-8-one hydrochloride, prepared as shown in Preparation 1 above, and 7.5 g of 5% Rh-Al$_2$O$_3$ in 300 ml of acetic acid was hydrogenated at 50 psi for 42 hours. The catalyst was removed by filtration and the filtrate was concentrated under reduced pressure. The residue was partitioned between methylene chloride and aqueous NH$_4$OH and the methylene chloride layer was separated and the solvent removed under reduced pressure. The residue was purified by silica gel chromatography, eluting with from 5–20% methanol in methylene chloride. The first component eluted was (±)-5,6,8aβ,9,10,11,12,12aβ,13,-13aα-decahydroisoquino[2,1-g][1,6]naphthyridin-8-one (9.7 g), (VI), m.p. 105°–106° C. The second component eluted was (±)-5,6,8aα,9,10,11,12,12aα,13,13aα-decahydroisoquino[2,1-g][1,6]naphthyridin-8-one (11.0 g), (V), m.p. 91°–92° C.

B. Similarly, replacing (±)-5,6,13,13a-tetrahydroisoquino[2,1-g][1,6]naphthyridine-8-one hydrochloride with the appropriate compound of formula (IV) and following the procedure in paragraph A above, the following compounds of formula (V) and (VI) were prepared:

(±)-3-methoxy-5,6,8aβ,9,10,11,12,12aβ,13,13aα-decahydroisoquino[2,1-g][1,6]naphthyridin-8-one; and (±)-3-methoxy-5,6,8aα,9,10,11,12,12aα,13,13aα-decahydroisoquino[2,1-g][1,6]naphthyridin-8-one, m.p. 118°–119° C.;

(±)-2,3-dimethoxy-5,6,8aβ,9,10,11,12,12aβ,13,13aα-decahydroisoquino[2,1-g][1,6]naphthyridin-8-one; and (±)-2,3-dimethoxy-5,6,8aα,9,10,11,12,12aα,13,13aα-decahydroisoquino[2,1-g][1,6]naphthyridin-8-one;

(±)-1,4-dimethoxy-5,6,8aβ,9,10,11,12,12aβ,13,13aα-decahydroisoquino[2,1-g][1,6]naphthyridin-8-one; and (±)-1,4-dimethoxy-5,6,8aα,9,10,11,12,12aα,13,13aα-decahydroisoquino[2,1-g][1,6]naphthyridin-8-one;

(±)-2,3-methylenedioxy-5,6,8aβ,9,10,11,12,12aβ,13,-13aα-decahydroisoquino[2,1-g][1,6]naphthyridin-8-one; and (±)-2,3-methylenedioxy-5,6,8aα,9,10,11,12,12aα,13,-13aα-decahydroisoquino[2,1-g][1,6]naphthyridin-8-one;

(±)-2,3-(ethylene-1,2-dioxy)-5,6,8aβ,9,10,11,12,-12aβ,13,13aα-decahydroisoquino[2,1-g][1,6]naphthyridin8-one; and (±)-2,3-(ethylene-1,2-dioxy)-5,6,8aα,9,10,11,12,-12aα,13,13aα-decahydroisoquino[2,1-g][1,6]naphthyridin8-one.

C. Similarly, replacing (±)-5,6,13,13a-tetrahydroisoquino[2,1-g][1,6]naphthyridine-8-one hydrochloride with other compounds of formula (IV) and following the procedure in paragraph A above, the following exemplary compounds of formula (V) and (VI) are prepared:

(±)-1-methyl-5,6,8aβ,9,10,11,12,12aβ,13,13aα-decahydroisoquino[2,1-g][1,6]naphthyridin-8-one; and
(±)-1-methyl-5,6,8aα,9,10,11,12,12aα,13,13aα-decahydroisoquino[2,1-g][1,6]naphthyridin-8-one;
(±)-2-methyl-5,6,8aβ,9,10,11,12,12aβ,13,13aα-decahydroisoquino[2,1-g][1,6]naphthyridin-8-one; and
(±)-2-methyl-5,6,8aα,9,10,11,12,12aα,13,13aα-decahydroisoquino[2,1-g][1,6]naphthyridin-8-one;
(±)-3-methyl-5,6,8aβ,9,10,11,12,12aβ,13,13aα-decahydroisoquino[2,1-g][1,6]naphthyridin-8-one; and
(±)-3-methyl-5,6,8aα,9,10,11,12,12aα,13,13aα-decahydroisoquino[2,1-g][1,6]naphthyridin-8-one;
(±)-2,3-dimethyl-5,6,8aβ,9,10,11,12,12aβ,13,13aα-decahydroisoquino[2,1-g][1,6]naphthyridine-8-one; and
(±)-2,3-dimethyl-5,6,8aα,9,10,11,12,12aα,13,13aα-decahydroisoquino[2,1-g][1,6]naphthyridin-8-one;
(±)-3-ethyl-5,6,8aβ,9,10,11,12,12aβ,13,13aα-decahydroisoquino[2,1-g][1,6]naphthyridin-8-one; and
(±)-3-ethyl-5,6,8aα,9,10,11,12,12aα,13,13aα-decahydroisoquino[2,1-g][1,6]naphthyridin-8-one;
(±)-3-isobutyl-5,6,8aβ,9,10,11,12,12aβ,13,13aα-decahydroisoquino[2,1-g][1,6]naphthyridin-8one; and
(±)-3-isobutyl-5,6,8aα,9,10,11,12,12aα,13,13aα-decahydroisoquino[2,1-g][1,6]naphthyridin-8-one;
(±)-3-n-hexyl-5,6,8aβ,9,10,11,12,12aβ,13,13aα-decahydroisoquino[2,1-g][1,6]naphthyridin-8-one; and
(±)-3-n-hexyl-5,6,8aα,9,10,11,12,12aα,13,13aα-decahydroisoquino[2,1-g][1,6naphthyridin-8-one;
(±)-1-methoxy-5,6,8aβ,9,10,11,12,12aβ,13,13aα-decahydroisoquino[2,1-g][1,6]naphthyridin-8-one; and
(±)-1-methoxy-5,6,8aα,9,10,11,12,12aα,13,13aα-decahydroisoquino[2,1-g][1,6]naphthyridin-8-one;
(±)-2-methoxy-5,6,8aβ,9,10,11,12,12aβ,13,13aα-decahydroisoquino[2,1-g][1,6]naphthyridin-8-one; and
(±)-2-methoxy-5,6,8aα,9,10,11,12,12aα,13,13aα-decahydroisoquino[2,1-g][1,6]naphthyridin-8-one;
(±)-4-methoxy-5,6,8aβ,9,10,11,12,12aβ,13,13aα-decahydroisoquino[2,1-g][1,6]naphthyridin-8-one; and
(±)-4-methoxy-5,6,8aα,9,10,11,12,12aα,13,13aα-decahydroisoquino[2,1-g][1,6]naphthyridin-8-one;
(±)-3-ethoxy-5,6,8aβ,9,10,11,12,12aβ,13,13aα-decahydroisoquino[2,1-g][1,6]naphthyridin-8-one; and
(±)-3-ethoxy-5,6,8aα,9,10,11,12,12aα,13,13aα-decahydroisoquino[2,1-g][1,6]naphthyridin-8-one;
(±)-3-isobutyl-5,6,8aβ,9,10,11,12,12aβ,13,13aα-decahydroisoquino[2,1-g][1,6]naphthyridin-8-one; and
(±)-3-isobutoxy-5,6,8aα,9,10,11,12,12aα,13,13aα-decahydroisoquino[2,1-g][1,6]naphthyridin-8-one;
(±)-3-n-hexyloxy-5,6,8aβ,9,10,11,12,12aβ,13,13aα-decahydroisoquino[2,1-g][1,6]naphthyridin-8-one; and
(±)-3-n-hexyloxy-5,6,8aα,9,10,11,12,12aα,13,13aα-decahydroisoquino[2,1-g][1,6]naphthyridin-8-one;
(±)-3-hydroxy-5,6,8aβ,9,10,11,12,12aβ,13,13aα-decahydroisoquino[2,1-g][1,6]naphthyridin-8-one; and
(±)-3-hydroxy-5,6,8aα,9,10,11,12,12aα,13,13aα-decahydroisoquino[2,1-g][1,6]naphthyridin-8-one;
(±)-2,3-dihydroxy-5,6,8aβ,9,10,11,12,12aβ,13,13aα-decahydroisoquino[2,1-g][1,6]naphthyridin-8-one; and
(±)-2,3-dihydroxy-5,6,8aα,9,10,11,12,12aα,13,13aα-decahydroisoquino[2,1-g][1,6]naphthyridin-8-one;
(±)-1,2-dimethoxy-5,6,8aβ,9,10,11,12,12aβ,13,13aα-decahydroisoquino[2,1-g][1,6]naphthyridin-8-one; and
(±)-1,2-dimethoxy-5,6,8aα,9,10,11,12,12aα,13,13aα-decahydroisoquino[2,1-g][1,6]naphthyridin-8-one;
(±)-1,4-dimethoxy-5,6,8aβ,9,10,11,12,12aβ,13,13aα-decahydroisoquino[2,1-g][1,6]naphthyridin-8-one; and
(±)-1,4-dimethoxy-5,6,8aα,9,10,11,12,12aα,13,13aα-decahydroisoquino[2,1-g][1,6]naphthyridin-8-one;
(±)-3,4-dimethoxy-5,6,8aβ,9,10,11,12,12aβ,13,13aα-decahydroisoquino[2,1-g][1,6]naphthyridin-8-one; and
(±)-3,4-dimethoxy-5,6,8aα,9,10,11,12,12aα,13,13aα-decahydroisoquino[2,1-g][1,6]naphthyridin-8-one;
(±)-2,3-diethoxy-5,6,8aβ,9,10,11,12,12aβ,13,13aα-decahydroisoquino[2,1-g][1,6]naphthyridin-8-one; and
(±)-2,3-diethoxy-5,6,8aα,9,10,11,12,12aα,13,13aα-decahydroisoquino[2,1-g][1,6]naphthyridin-8-one;
(±)-2,3-di-n-butoxy-5,6,8aβ,9,10,11,12,12aβ,13,13aα-decahydroisoquino[2,1-g][1,6]naphthyridin-8-one; and
(±)-2,3-di-n-butoxy-5,6,8aα,9,10,11,12,12aα,13,13aα-decahydroisoquino[2,1-g][1,6]naphthyridin-8-one;
(±)-1,2-methylenedioxy-5,6,8aβ,9,10,11,12,12aβ,13,13aα-decahydroisoquino[2,1-g][1,6]naphthyridin-8-one; and
(±)-1,2-methylenedioxy-5,6,8-aα,9,10,11,12,12aα,13,13aα-decahydroisoquino[2,1-g][1,6]naphthyridin-8-one;
(±)-2-chloro-5,6,8aβ,9,10,11,12,12aβ,13,13aα-decahydroisoquino[2,1-g][1,6]naphthyridin-8-one; and
(±)-2-chloro-5,6,8aα,9,10,11,12,12aα,13,13aα-decahydroisoquino[2,1-g][1,6]naphthyridin-8-one;
(±)-3-chloro-5,6,8aβ,9,10,11,12,12aβ,13,13aα-decahydroisoquino[2,1-g][1,6]naphthyridin-8-one; and
(±)-3-chloro-5,6,8aα,9,10,11,12,12aα,13,13aα-decahydroisoquino[2,1][1,6]naphthyridin-8-one;
(±)-4-chloro-5,6,8aβ,9,10,11,12,12aβ,13,13aα-decahydroisoquino[2,1-g][1,6]naphthyridin-8-one; and
(±)-4-chloro-5,6,8aα,9,10,11,12,12aα,13,13aα-decahydroisoquino[2,1-g][1,6]naphthyridin-8-one;
(±)-3-bromo-5,6,8aβ,9,10,11,12,12aβ,13,13aα-decahydroisoquino[2,1-g][1,6]naphthyridin-8-one; and
(±)-3-bromo-5,6,8aα,9,10,11,12,12aα,13,13aα-decahydroisoquino[2,1-g][1,6]naphthyridin-8-one;
(±)-3-fluoro-5,6,8aβ,9,10,11,12,12aβ,13,13aα-decahydroisoquino[2,1-g][1,6]naphthyridin-8-one; and
(±)-3-fluoro-5,6,8aα,9,10,11,12,12aα,13,13aα-decahydroisoquino[2,1-g][1,6]naphthyridin-8-one;
(±)-2-fluoro-5,6,8aβ,9,10,11,12,12aβ,13,13aα-decahydroisoquino[2,1-g][1,6]naphthyridin-8-one; and
(±)-2-fluoro-5,6,8aα,9,10,11,12,12aα,13,13aα-decahydroisoquino[2,1-g][1,6]naphthyridin-8-one;

PREPARATION 3

Preparation of
(±)-5,6,8aβ,9,10,11,12,12aβ,13,13aα-Decahydro-8H-isoquino[2,1 g][1,6]naphthyridine and Related Compounds of formula (VII) and (VIII)

A. A solution of 9.6 g of (±)-5,6,8aβ,9,10,11,12,12aβ,13,13aα-decahydroisoquino[2,1-g][1,6]naphthyridin-8-one (V), prepared as shown in Preparation 2, in 50 ml of tetrahydrofuran was added slowly to a solution of 2.5 g of lithium aluminum hydride in 75 ml of tetrahydrofuran. The resulting mixture was stirred at reflux for 3 hours, cooled, and treated sequentially with 2.5 ml of water, 2.5 ml of 15% sodium hydroxide, and 7.5 ml of water. The mixture was filtered and the filtrate was evaporated to afford 8.8 g of (±)-5,6,8aβ,9,10,11,12,-12aβ,13,13aα-decahydro-8H-isoquino[2,1-g][1,6]naphthyridine (VII) as a thick oil. The oil was dissolved in ethanol and acidified with anhydrous HCl in ether, from which a dihydrochloride salt was crystallized, m.p. 290°-295° C.

B. Similarly, replacing (±)-5,6,8aα,9,10,11,12,-12aα,13,13aα-decahydro-8H-isoquino[2,1-g][1,6]naphthyridine;

(±)-3-methoxy-5,6,8aβ,9,10,11,12,12aβ,13,13aα-decahydro-8H-isoquino[2,1-g][1,6]naphthyridine;
(±)-3-methoxy-5,6,8aα,9,10,11,12,12aα,13,13aα-decahydro-8H-isoquino[2,1-g][1,6]naphthyridine;
(±)-2,3-dimethoxy-5,6,8aβ,9,10,11,12,12aβ,13,13aα-decahydro-8H-isoquino[2,1-g][1,6]naphthyridine;
(±)-2,3-dimethoxy-5,6,8aα,9,10,11,12,12aα,13,13aα-decahydro-8H-isoquino[2,1-g][1,6]naphthyridine;
(±)-1,4-dimethoxy-5,6,8aβ,9,10,11,12,12aβ,13,13aα-decahydro-8H-isoquino[2,1-g][1,6]naphthyridine;
(±)-1,4-dimethoxy-5,6,8aα,9,10,11,12,12aα,13,13aα-decahydro-8H-isoquino[2,1-g][1,6]naphthyridine;
(±)-2,3-methylenedioxy-5,6,8aβ,9,10,11,12,12aβ,13,-13aα-decahydro-8H-isoquino[2,1-g][1,6]naphthyridine; and
(±)-2,3-methylenedioxy-5,6,8aα,9,10,11,12,12aα,13,-13aα-decahydro-8H-isoquino[2,1-g][1,6]naphthyridine;
(±)-2,3-(ethylene-1,2-dioxy)-5,6,8aβ,9,10,11,12,-12aβ,13,13aα-decahydro-8H-isoquino[2,1-g][1,6]naphthyridine; and
(±)-2,3-(ethylene-1,2-dioxy)-5,6,8aα,9,10,11,12,-12aα,13,13aα-decahydro-8H-isoquino[2,1-g][1,6]naphthyridine;

C. Similarly, replacing (±)-5,6,8aβ,9,10,11,12,12aβ,13,13aα-decahydroisoquino[2,1-g][1,6]naphthyridin-8-one with other compounds of formula (V) or (VI) and following the procedure in paragraph A above, the following exemplary compounds of formula (VII) and (VIII) are prepared:

(±)-1-methyl-5,6,8aβ,9,10,11,12,12aβ,13,13aα-decahydro-8H-isoquino[2,1-g][1,6]naphthyridine; and
(±)-1-methyl-5,6,8aα,9,10,11,12,12aα,13,13aα-decahydro-8H-isoquino[2,1-g][1,6]naphthyridine;
(±)-2-methyl-5,6,8aβ,9,10,11,12,12aβ,13,13aα-decahydro-8H-isoquino[2,1-g][1,6]naphthyridine; and
(±)-2-methyl-5,6,8aα,9,10,11,12,12aα,13,13aα-decahydro-8H-isoquino[2,1-g][1,6]naphthyridine;
(±)-3-methyl-5,6,8aβ,9,10,11,12,12aβ,13,13aα-decahydro-8H-isoquino[2,1-g][1,6]naphthyridine; and
(±)-3-methyl-5,6,8aα,9,10,11,12,12aα,13,13aα-decahydro-8H-isoquino[2,1-g][1,6]naphthyridine;
(±)-2,3-dimethyl-5,6,8aβ,9,10,11,12,12aβ,13,13aα-decahydro-8H-isoquino[2,1-g][1,6]naphthyridine; and
(±)-2,3-dimethyl-5,6,8aα,9,10,11,12,12aα,13,13aα-decahydro-8H-isoquino[2,1-g][1,6]naphthyridine;
(±)-3-ethyl-5,6,8aβ,9,10,11,12,12aβ,13,13aα-decahydro-8H-isoquino[2,1-g][1,6]naphthyridine; and
(±)-3-ethyl-5,6,8aα,9,10,11,12,12aα,13,13aα-decahydro-8H-isoquino[2,1-g][1,6]naphthyridine;
(±)-3-isobutyl-5,6,8aβ,9,10,11,12,12aβ,13,13aα-decahydro-8H-isoquino[2,1-g][1,6]naphthyridine; and
(±)-3-isobutyl-5,6,8aα,9,10,11,12,12aα,13,13aα-decahydro-8H-isoquino[2,1-g][1,6]naphthyridine;
(±)-3-n-hexyl-5,6,8aβ,9,10,11,12,12aβ,13,13aα-decahydro-8H-isoquino[2,1-g][1,6]naphthyridine; and
(±)-3-n-hexyl-5,6,8aα,9,10,11,12,12aα,13,13aα-decahydro-8H-isoquino[2,1-g][1,6]naphthyridine;
(±)-1-methoxy-5,6,8aβ,9,10,11,12,12aβ,13,13aα-decahydro-8H-isoquino[2,1-g][1,6]naphthyridine; and
(±)-1-methoxy-5,6,8aα,9,10,11,12,12aα,13,13aα-decahydro-8H-isoquino[2,1-g][1,6]naphthyridine;
(±)-2-methoxy-5,6,8aβ,9,10,11,12,12aβ,13,13aα-decahydro-8H-isoquino[2,1-g][1,6]naphthyridine; and
(±)-2-methoxy-5,6,8aα,9,10,11,12,12aα,13,13aα-decahydro-8H-isoquino[2,1-g][1,6]naphthyridine;
(±)-4-methoxy-5,6,8aβ,9,10,11,12,12aβ,13,13aα-decahydro-8H-isoquino[2,1-g][1,6]naphthyridine; and
(±)-4-methoxy-5,6,8aα,9,10,11,12,12aα,13,13aα-decahydro-8H-isoquino[2,1-g][1,6]naphthyridine;
(±)-3-ethoxy-5,6,8aβ,9,10,11,12,12aβ,13,13aα-decahydro-8H-isoquino[2,1-g][1,6]naphthyridine; and
(±)-3-ethoxy-5,6,8aα,9,10,11,12,12aα,13,13aα-decahydro-8H-isoquino[2,1-g][1,6]naphthyridine;
(±)-3-isobutoxy-5,6,8aβ,9,10,11,12,12aβ,13,13aα-decahydro-8H-isoquino[2,1-g][1,6]naphthyridine; and
(±)-3-isobutoxy-5,6,8aα,9,10,11,12,12aα,13,13aα-decahydro-8H-isoquino[2,1-g][1,6]naphthyridine;
(±)-3-n-hexyloxy-5,6,8aβ,9,10,11,12,12aβ,13,13aα-decahydro-8H-isoquino[2,1-g][1,6]naphthyridine; and
(±)-3-n-hexyloxy-5,6,8aα,9,10,11,12,12aα,13,13aα-decahydro-8H-isoquino[2,1-g][1,6]naphthyridine;
(±)-3-hydroxy-5,6,8aβ,9,10,11,12,12aβ,13,13aα-decahydro-8H-isoquino[2,1-g][1,6]naphthyridine; and
(±)-3-hydroxy-5,6,8aα,9,10,11,12,12aα,13,13aα-decahydro-8H-isoquino[2,1-g][1,6]naphthyridine;
(±)-2,3-dihydroxy-5,6,8aβ,9,10,11,12,12aβ,13,13aα-decahydro-8H-isoquino[2,1-g][1,6]naphthyridine; and
(±)-2,3-dihydroxy-5,6,8aα,9,10,11,12,12aα,13,13aα-decahydro-8H-isoquino[2,1-g][1,6]naphthyridine;
(±)-1,2-dimethoxy-5,6,8aβ,9,10,11,12,12aβ,13,13aα-decahydro-8H-isoquino[2,1-g][1,6]naphthyridine; and
(±)-1,2-dimethoxy-5,6,8aα,9,10,11,12,12aα,13,13aα-decahydro-8H-isoquino[2,1-g][1,6]naphthyridine;
(±)-1,4-dimethoxy-5,6,8aβ,9,10,11,12,12aβ,13,13aα-decahydro-8H-isoquino[2,1-g][1,6]naphthyridine; and
(±)-1,4-dimethoxy-5,6,8aα,9,10,11,12,12aα,13,13aα-decahydro-8H-isoquino[2,1-g][1,6]naphthyridine;
(±)-3,4-dimethoxy-5,6,8aβ,9,10,11,12,12aβ,13,13aα-decahydro-8H-isoquino[2,1-g][1,6]naphthyridine; and
(±)-3,4-dimethoxy-5,6,8aα,9,10,11,12,12aα,13,13aα-decahydro-8H-isoquino[2,1-g][1,6]naphthyridine;
(±)-2,3-diethoxy-5,6,8aβ,9,10,11,12,12aβ,13,13aα-decahydro-8H-isoquino[2,1-g][1,6]naphthyridine; and
(±)-2,3-diethoxy-5,6,8aα,9,10,11,12,12aα,13,13aα-decahydro-8H-isoquino[2,1-g][1,6]naphthyridine;
(±)-2,3-di-n-butoxy-5,6,8aβ,9,10,11,12,12aβ,13,13aα-decahydro-8H-isoquino[2,1-g][1,6]naphthyridine; and (±)-2,3-di-n-butoxy-5,6,8aα,9,10,11,12,12aα,13,13aα-decahydro-8H-isoquino[2,1-g][1,6]naphthyridine;

(±)-1,2-methylenedioxy-5,6,8aβ,9,10,11,12,12aβ,13,13aα-decahydro-8H-isoquino[2,1-g][1,6]naphthyridine; and (±)-1,2-methylenedioxy-5,6,8aα,9,10,11,12,12aα,13,13aα-decahydro-8H-isoquino[2,1-g][1,6]naphthyridine;

(±)-2-chloro-5,6,8aα,9,10,11,12,12aβ,13,13aα-decahydro-8H-isoquino[2,1-g][1,6]naphthyridine; and (±)-2-chloro-5,6,8aα,9,10,11,12,12aα,13,13aα-decahydro-8H-isoquino[2,1-g][1,6]naphthyridine;

(±)-3-chloro-5,6,8aβ,9,10,11,12,12aβ,13,13aα-decahydro-8H-isoquino[2,1-g][1,6]naphthyridine; and (±)-3-chloro-5,6,8aα,9,10,11,12,12aα,13,13aα-decahydro-8H-isoquino[2,1-g][1,6]naphthyridine;

(±)-4-chloro-5,6,8aβ,9,10,11,12,12aβ,13,13aα-decahydro-8H-isoquino[2,1-g][1,6]naphthyridine; and (±)-4-chloro-5,6,8aα,9,10,11,12,12aα,13,13aα-decahydro-8H-isoquino[2,1-g][1,6]naphthyridine;

(±)-3-bromo-5,6,8aβ,9,10,11,12,12aβ,13,13aα-decahydro-8H-isoquino[2,1-g][1,6]naphthyridine; and (±)-3-bromo-5,6,8aα,9,10,11,12,12aα,13,13aα-decahydro-8H-isoquino[2,1-g][1,6]naphthyridine;

(±)-3-fluoro-5,6,8aβ,9,10,11,12,12aβ,13,13aα-decahydro-8H-isoquino[2,1-g][1,6]naphthyridine; and (±)-3-fluoro-5,6,8aα,9,10,11,12,12aα,13,13aα-decahydro-8H-isoquino[2,1-g][1,6]naphthyridine;

(±)-2-fluoro-5,6,8aβ,9,10,11,12,12aβ,13,13aα-decahydro-8H-isoquino[2,1-g][1,6]naphthyridine; and (±)-2-fluoro-5,6,8aα,9,10,11,12,12aα,13,13aα-decahydro-8H-isoquino[2,1-g][1,6]-naphthyridine;

EXAMPLE 1

Preparation of (±)-12-Methanesulfonyl-5,6,8aα,9,10,11,12,12aα,13,13aα-decahydro-8H-isoquino[2,1-g][1,6]naphthyridine hydrochloride and Related Compounds of Formula (1) and (2)

A. A solution of 0.4 g of (±)-5,6,8aα,9,10,11,12,12aα,13,13aα-decahydro-8H-isoquino[2,1-g][1,6]naphthyridine (VII) in 15 ml of methylene chloride and 0.5 ml of triethylamine was cooled in an ice bath and 0.5 ml of methanesulfonyl chloride was added. The mixture was stirred at room temperature for 1 hour, diluted with 100 ml of ether, and extracted with dilute HCl. The aqueous HCl layer was basified with NH₄OH and extracted with methylene chloride. The methylene chloride was evaporated to a residue which was dissolved in ethanol and acidified with ethanolic HCl. Crystallization was induced by adding a small amount of diethylether. Filtration afforded 0.4 g of (±)-12-methanesulfonyl-5,6,8aα,9,10,11,12,12aα,13,13aα-decahydro-8H-isoquino[2,1-g][1,6]naphthyridine hydrochloride, m.p. 234°–235° C.

B. Similarly, replacing (±)-5,6,8aα,9,10,11,12,12aα,13,13aα-decahydro-8H-isoquino[2,1-g][1,6]naphthyridine with the appropriate compound of formula (VII) or (VIII), optionally replacing methanesulfonyl chloride with other sulfonyl halides of formula ZSO₂R, where Z is chlorine or bromine and R is as defined supra, and following the procedure in paragraph A above, the following compounds of formula (1) and (2) were prepared:

(±)-12-methanesulfonyl-5,6,8aβ,9,10,11,12,12aβ,13,13aα-decahydro-8H-isoquino[2,1-g][1,6]naphthyridine hydrochloride, m.p. 230°–235° C.;

(±)-12-(1-butanesulfonyl)-5,6,8aβ,9,10,11,12,12aβ,13,13aα-decahydro-8H-isoquino[2,1-g][1,6]naphthyridine hydrochloride, m.p. 215°–216° C.;

(±)-12-ethanesulfonyl-5,6,8aα,9,10,11,12,12aα,13,13aα-decahydro-8H-isoquino[2,1-g][1,6]naphthyridine hydrochloride, m.p. 203°–204° C.;

(±)-3-methoxy-12-methanesulfonyl-5,6,8aα,9,10,11,12,12,aα,13,13aα-decahydro-8H-isoquino[2,1-g][1,6]naphthyridine hydrochloride, m.p. 265°–266° C.;

(±)-3-methoxy-12-methanesulfonyl-5,6,8aβ,9,10,11,12,12aβ,13,13aα-decahydro-8H-isoquino[2,1-g][1,6]naphthyridine hydrochloride, m.p. 238°–239° C.;

(±)-3-methoxy-12-(2-methylpropanesulfonyl)-5,6,8aα,9,10,11,12,12aα,13,13aα-decahydro-8H-isoquino[2,1-g][1,6]naphthyridine hydrochloride, m.p. 127°–130° C.;

(±)-2,3-dimethoxy-12-methanesulfonyl-5,6,8aα,9,10,11,12,12aα,13,13aα-decahydro-8H-isoquino[2,1-g][1,6]naphthyridine hydrochloride, m.p. 175°–177° C.;

(±)-1,4-dimethoxy-12-methanesulfonyl-5,6,8aα,9,10,11,12,12aα,13,13aα-decahydro-8H-isoquino[2,1-g][1,6]naphthyridine hydrochloride, m.p.194°–195° C.;

(±)-2,3-dimethoxy-12-(2-methylpropanesulfonyl)-5,6,8aα,9,10,11,12,12aα,13,13aα-decahydro-8H-isoquino[2,1-g][1,6]naphthyridine hydrochloride, m.p. 155°–156° C.;

(±)-2,3-methylenedioxy-12-methanesulfonyl-5,6,8aα,9,10,11,12,12aα,13,13aα-decahydro-8H-isoquino[2,1-g][1,6]naphthyridine hydrochloride, m.p. 279°–280° C.;

(±)-2,3-(ethylene-1,2-dioxy)-12-methanesulfonyl-5,6,8aα,9,10,11,12,12aα,13,13aα-decahydro-8H-isoquino[2,1-g][1,6]naphthyridine hydrochloride, m.p. 279°–280° C.;

(±)-2,3-methylenedioxy-12-(2-methylpropanesulfonyl)-5,6,8aα,9,10,11,12,12aα,13,13aα-decahydro-8H-isoquino[2,1-g][1,6]naphthyridine hydrochloride, m.p. 172°–174° C.;

(±)-12-(1-butanesulfonyl)-5,6,8aα,9,10,11,12,12aα,13,13aα-decahydro-8H-isoquino[2,1-g][1,6]naphthyridine hydrochloride, m.p. 220°–222° C.;

(±)-12-(1-propanesulfonyl)-5,6,8aα,9,10,11,12,12aα,13,13aα-decahydro-8H-isoquino[2,1-g][1,6]naphthyridine hydrochloride, m.p. 235°–236° C.;

(±)-12-(2-methylpropanesulfonyl)-5,6,8aα,9,10,11,12,12aα,13,13aα-decahydro-8H-isoquino[2,1-g][1,6]naphthyridine hydrochloride, m.p. 220°–221° C.;

(±)-12-phenylsulfonyl-5,6,8aα,9,10,11,12,12aα,13,13aα-decahydro-8H-isoquino[2,1-g][1,6]naphthyridine hydrochloride, m.p. 247°–248° C.;

(±)-12-(4-methoxyphenylsulfonyl)-5,6,8aα,9,10,11,12,12aα,13,13aα-decahydro-8H-isoquino[2,1-g][1,6]naphthyridine hydrochloride, m.p. 256°–257° C.;

(±)-12-(4-chlorophenylsulfonyl)-5,6,8aα,9,10,11,12,12aα,13,13aα-decahydro-8H-isoquino[2,1-g][1,6]naphthyridine hydrochloride, m.p. 261°–263° C.;

(±)-12-(4-fluorophenylsulfonyl)-5,6,8aα,9,10,11,12,12aα,13,13aα-decahydro-8H-isoquino[2,1g][1,6-]naphthyridine hydrochloride, m.p. 258°–259° C.;

(±)-12-(2-methoxyethanesulfonyl)-5,6,8aα,9,10,11,12,-12aα,13,13aα-decahydro-8H-isoquino[2,1-g][1,6]naphthyridine hydrochloride, m.p. 173° ∝ 174° C.;

(±)-3-methoxy-12-(2-methoxyethanesulfonyl)-5,6,8aα,9,10,11,12,12aα,13,13aα-decahydro-8H-isoquino[2,1-g][1,6]naphthyridine hydrochloride, m.p. 173°-174° C.; and (±)-12-(N,N-dimethylaminosulfonyl)-5,6,8aα,9,10,11,12,12aα,13,13aα-decahydro-8H-isoquino[2,1-g][1,6]naphthyridine hydrochloride, m.p. 237°-238° C.

C. Similarly, replacing (±)-5,6,8aα,9,10,11,12,-12aα,13,13aα-decahydro-8H-isoquino[2,1-g][1,6]naphthyridine with other compounds of formula (VII) or (VIII), optionally replacing methanesulfonyl chloride with other sulfonyl halides of formula $ZSO_2R$ and following the procedure in paragraph A above, the following compounds of formula (1) and (2) are prepared:

(±)-12-ethanesulfonyl-5,6,8aβ,9,10,11,12,12aβ,13,-13aα-decahydro-8H-isoquino[2,1-g][1,6]naphthyridine hydrochloride;

(±)-3-methoxy-12-(2-methylpropanesulfonyl)-5,6,8aβ-9,10,11,12,12aβ,13,13aα-decahydro-8H-isoquino[2,1-g][1,6]naphthyridine hydrochloride;

(±)-2,3-dimethoxy-12-methanesulfonyl-5,6,8aβ,9,10,11,12,12aβ,13,13aα-decahydro-8H-isoquino[2,1-g][1,6]naphthyridine hydrochloride;

(±)-2,3-dimethoxy-12-(2-methylpropanesulfonyl)-5,6,8aβ,9,10,11,12,12aβ,13,13aα-decahydro-8H-isoquino[2,1-g][1,6]naphthyridine hydrochloride;

(±)-2,3-methylenedioxy-12-methanesulfonyl-5,6,8aβ,9,10,11,12,12aβ,13,13aα-decahydro-8H-isoquino[2,1-g][1,6]naphthyridine hydrochloride;

(±)-2,3-methylenedioxy-12-(2-methylpropanesulfonyl)-5,6,8aβ,9,10,11,12,12aβ,13,13aα-decahydro-8H-isoquino[2,1-g][1,6]naphthyridine hydrochloride;

(±)-12-(2-methylpropanesulfonyl)5,6,8aβ,9,10,11,12,-12aβ,13,13aα-decahydro-8H-isoquino[2,1-g][1,6]naphthyridine hydrochloride;

(±)-12-phenylsulfonyl-5,6,8aβ,9,10,11,12,12aβ,13,-13aα-decahydro-8H-isoquino[2,1-g][1,6]naphthyridine hydrochloride;

(±)-12-(4-methoxyphenylsulfonyl)-5,6,8aβ,9,10,11,12,-12aβ,13,13aα-decahydro-8H-isoquino[2,1-g][1,6]naphthyridine hydrochloride;

(±)-12-(4-chlorophenylsulfonyl)-5,6,8aβ,9,10,11,12,-12aβ,13,13aα-decahydro-8H-isoquino[2,1-g][1,6]naphthyridine hydrochloride;

(±)-12-(4-aminophenylsulfonyl)-5,6,8aβ,9,10,11,12,-12aβ,13,13aα-decahydro-8H-isoquino[2,1-g][1,6]naphthyridine hydrochloride;

(±)-12-(4-fluorophenylsulphonyl)-5,6,8aβ,9,10,11,12,-12aβ,13,13aα-decahydro-8H-isoquino[2,1-g][1,6]naphthyridine hydrochloride;

(±)-12-(2-methoxyethanesulfonyl)-5,6,8aβ,9,10,11,12,-12aβ,13,13aα-decahydro-8H-isoquino[2,1-g][1,6]naphthyridine hydrochloride;

(±)-12-(2-hydroxyethanesulfonyl)-5,6,8aβ,9,10,11,12,-12aβ,13,13aα-decahydro-8H-isoquino[2,1-g][1,6]naphthyridine hydrochloride;

(±)-12-(N,N-dimethylaminosulfonyl)-5,6,8aβ,9,10,11,12,12aβ,13,13aα-decahydro-8H-isoquino[2,1-g][1,6]naphthyridine hydrochloride;

(±)-3-methyl-12-methanesulfonyl-5,6,8aα,9,10,11,12,-12aα,13,13aα-decahydro-8H-isoquino[2,1-g][1,6]naphthyridine hydrochloride;

(±)-2-methyl-12-methanesulfonyl-5,6,8aβ,9,10,11,12,-12aβ,13,13aα-decahydro-8H-isoquino[2,1-g][1,6naphthyridine hydrochloride;

(±)-2,3-dimethyl-12-methanesulfonyl-5,6,8aα,9,10,11,12,12aα,13,13aα-decahydro-8H-isoquino[2,1-g][1,6]naphthyridine hydrochloride;

(±)-2,3-dimethyl-12-methanesulfonyl-5,6,8aβ,9,10,11,12,12aβ,13,13aα-decahydro-8H-isoquino[2,1-g][1,6]naphthyridine hydrochloride;

(±)-2-n-hexyl-12-methanesulfonyl-5,6,8aα,9,10,11,12,-12aα,13,13aα-decahydro-8H-isoquino[2,1-g][1,6]naphthyridine hydrochloride;

(±)-2-n-hexyl-12-methanesulfonyl-5,6,8aβ,9,10,11,12,-12aβ,13,13aα-decahydro-8H-isoquino[2,1-g][1,6]naphthyridine hydrochloride;

(±)-2-methoxy-12-methanesulfonyl-5,6,8aα,9,10,11,12,-12aα,13,13aα-decahydro-8H-isoquino[2,1-g][1,6]naphthyridine hydrochloride;

(±)-2-methoxy-12-methanesulfonyl-5,6,8aβ,9,10,11,12,-12aβ,13,13aα-decahydro-8H-isoquino[2,1-g][1,6]naphthyridine hydrochloride;

(±)-3-ethoxy-12-methanesulfonyl-5,6,8aα,9,10,11,12,-12aα,13,13aα-decahydro-8H-isoquino[2,1-g][1,6]naphthyridine hydrochloride;

(±)-3-ethoxy-12-methanesulfonyl-5,6,8aβ,9,10,11,12,-12aβ,13,13aα-decahydro-8H-isoquino[2,1-g][1,6]naphthyridine hydrochloride;

(±)-3-isobutoxy-12-methanesulfonyl-5,6,8aα,9,10,11,12,12aα,13,13aα-decahydro-8H-isoquino[2,1-g][1,6]naphthyridine hydrochloride;

(±)-3-isobutoxy-12-methanesulfonyl-5,6,8aβ,9,10,11,12,12aβ,13,13aα-decahydro-8H-isoquino[2,1-g][1,6]naphthyridine hydrochloride;

(±)-3-n-hexyloxy-12-methanesulfonyl-5,6,8aα,9,10,11,12,12aα,13,13aα-decahydro-8H-isoquino[2,1g][1,6]naphthyridine hydrochloride;

(±)-3-n-hexyloxy-12-methanesulfonyl-5,6,8aβ,9,10,11,12,12aβ,13,13aα-decahydro-8H-isoquino[2,1-g][1,6]naphthyridine hydrochloride;

(±)-3-hydroxy-12-methanesulfonyl-5,6,8aα,9,10,11,12,-12aα,13,13aα-decahydro-8H-isoquino[2,1-g][1,6]naphthyridine hydrochloride;

(±)-3hydroxy-12-methanesulfonyl-5,6,8aβ,9,10,11,12,-12aβ,13,13aα-decahydro-8H-isoquino[2,1-g][1,6]naphthyridine hydrochloride;

(±)-2,3-dihydroxy-12-methanesulfonyl-5,6,8aα,9,10,11,12,12aα,13,13aα-decahydro-8H-isoquino[2,1-g][1,6]naphthyridine hydrochloride;

(±)-2,3-dihydroxy-12-methanesulfonyl-5,6,8aβ,9,10,11,12,12aβ,13,13aα-decahydro-8H-isoquino[2,1-g][1,6]naphthyridine hydrochloride;

(±)-1,2-dimethoxy-12-methanesulfonyl-5,6,8aα,9,10,11,12,12aα,13,13aα-decahydro-8H-isoquino[2,1-g][1,6]naphthyridine hydrochloride;

(±)-1,2-dimethoxy-12-methanesulfonyl-5,6,8aβ,9,10,11,12,12aβ,13,13aα-decahydro-8H-isoquino[2,1-g][1,6]naphthyridine hydrochloride;

(±)-1,4-dimethoxy-12-methanesulfonyl-5,6,8aα,9,10,11,12,12aα,13,13aα-decahydro-8H-isoquino[2,1-g][1,6]naphthyridine hydrochloride;

(±)-1,4-dimethoxy-12-methanesulfonyl-5,6,8aβ,9,10,11,12,12aβ,13,13aα-decahydro-8H-isoquino[2,1-g][1,6]naphthyridine hydrochloride;

(±)-2,3-diethoxy-12-methanesulfonyl-5,6,8aα,9,10,11,12,12aα,13,13aα-decahydro-8H-isoquino[2,1-g][1,6]naphthyridine hydrochloride;

(±)-2,3-diethoxy-12-methanesulfonyl-
5,6,8aβ,9,10,11,12,12aβ,13,13aα-decahydro-8H-
isoquino[2,1-g][1,6]naphthyridine hydrochloride;
(±)-2,3-di-n-butoxy-12-methanesulfonyl-
5,6,8aα,9,10,11,12,12aα,13,13aα-decahydro-8H-
isoquino[2,1-g][1,6]napthyridine hydrochloride;
(±)-2,3di-n-butoxy-12-methanesulfonyl-
5,6,8aβ,9,10,11,12,12aβ,13,13aα-decahydro-8H-
isoquino[2,1-g][1,6]naphthyridine hydrochloride;
(±)-3,4-methylenedioxy-12-methanesulfonyl-
5,6,8aα,9,10,11,12,12aα,13,13aα-decahydro-8H-
isoquino[2,1-g][1,6]naphthyridine hydrochloride;
(±)-3,4-methylenedioxy-12-methanesulfonyl-
5,6,8aβ,9,10,11,12,12aβ,13,13aα-decahydro-8H-
isoquino[2,1-g][1,6]naphthyridine hydrochloride;
(±)-2-chloro-12-methanesulfonyl-5,6,8aα,9,10,11,12,-
12aα,13,13-decahydro-8H-isoquino[2,1-g][1,6]naph-
thyridine hydrochloride;
(±)-2-chloro-12-methanesulfonyl-5,6,8aβ,9,10,11,12,-
12aβ,13,13aα-decahydro-8H-isoquino[2,1-
g][1,6]naphthyridine hydrochloride;
(±)-3-chloro-12-methanesulfonyl-5,6,8aα,9,10,11,12,-
12aα,13,13aα-decahydro-8H-isoquino[2,1-
g][1,6]naphthyridine hydrochloride;
(±)-3-chloro-12-methanesulfonyl-5,6,8aβ,9,10,11,12,-
12aβ,13,13aα-decahydro-8H-isoquino[2,1-
g][1,6]naphthyridine hydrochloride;
(±)-3-fluoro-12-methanesulfonyl-5,6,8aα,9,10,11,12,-
12aα,13,13-decahydro-8H-isoquino[2,1-g][1,6]naph-
thyridine hydrochloride;
(±)-3-fluoro-12-methanesulfonyl-5,6,8aβ,9,10,11,12,-
12aβ,13,13aα-decahydro-8H-isoquino[2,1-
g][1,6]naphthyridine hydrochloride;
(±)-12-aminosulfonyl-5,6,8aα,9,10,11,12,12aα,13,13aα-
decahydro-8H-isoquino[2,1-g][1,6]naphthyridine hy-
drochloride;
(±)-12-aminosulfonyl-5,6,81β,9,10,11,12,12aβ,13,13aα-
decahydro-8H-isoquino[2,1-g][1,6]naphthyridine hy-
drochloride;
(±)-12-methylaminosulfonyl-5,6,8aα,9,10,11,12,-
12aα,13,13aα-decahydro-8H-isoquino[2,1-
g][1,6]naphthyridine hydrochloride;
(±)-12-methylaminosulfonyl-5,6,8aβ,9,10,11,12,-
12aβ,13,13aα-decahydro-8H-isoquino[2,1-
g][1,6]naphthyridine hydrochloride;
(±)-12-diethylaminosulfonyl-5,6,8aα,9,10,11,12,-
12aα,13,13aα-decahydro-8H-isoquino[2,1-
g][1,6]naphthyridine hydrochloride;
(±)-12-diethylaminosulfonyl-5,6,8aβ,9,10,11,12,-
12aβ,13,13aα-decahydro-8H-isoquino[2,1-
g][1,6]naphthyridine hydrochloride;
(±)-12-di-n-hexylaminosulfonyl-5,6,8aα,9,10,11,12,-
12aα,13,13aα-decahydro-8H-isoquino[2,1-
g][1,6]naphthyridine hydrochloride;
(±)-12-di-n-hexylaminosulfonyl-5,6,8aβ,9,10,11,12,-
12aβ,13,13aα-decahydro-8H-isoquino[2,1-
g][1,6]naphthyridine hydrochloride;
(±)-12-(1-piperazinosulfonyl)-5,6,8aα,9,10,11,12,-
12aα,13,13aα-decahydro-8H-isoquino[2,1-
g][1,6]naphthyridine hydrochloride;
(±)-12-(1-piperazinosulfonyl)-5,6,8aβ,9,10,11,12,-
12aβ,13,13aα-decahydro-8H-isoquino[2,1-
g][1,6]naphthyridine hydrochloride;
(±)-12-(1-morpholinosulfonyl)-5,6,8aα,9,10,11,12,-
12aα,13,13aα-decahydro-8H-isoquino[2,1-
g][1,6]naphthyridine hydrochloride;
(±)-12-(1-morpholinosulfonyl)-5,6,8aβ,9,10,11,12,-
12aβ,13,13aα-decahydro-8H-isoquino[2,1-
g][1,6]naphthyridine hydrochloride;
(±)-12-(1-piperidinosulfonyl)-5,6,8aα,9,10,11,12,-
12aα,13,13aα-decahydro-8H-isoquino[2,1-
g][1,6]naphthyridine hydrochloride;
(±)-12-(1-piperidinosulfonyl)-5,6,8aβ,9,10,11,12,-
12aβ,13,13aα-decahydro-8H-isoquino[2,1-
g][1,6]naphthyridine hydrochloride;
(±)-3-methyl-12-ethanesulfonyl-5,6,8aα,9,10,11,12,-
12aα,13,13aα-decahydro-8H-isoquino[2,1-
g][1,6]naphthyridine hydrochloride;
(±)-3-methyl-12-ethanesulfonyl-5,6,8aβ,9,10,11,12,-
12aβ,13,13aα-decahydro-8H-isoquino[2,1-
g][1,6]naphthyridine hydrochloride;
(±)-3-ethoxy-12-ethanesulfonyl-5,6,8aα,9,10,11,12,-
12aα,13,13aα-decahydro-8H-isoquino[2,1-
g][1,6]naphthyridine hydrochloride;
(±)-3-ethoxy-12-ethanesulfonyl-5,6,8aβ,9,10,11,12,-
12aβ,13,13aα-decahydro-8H-isoquino[2,1-
g][1,6]naphthyridine hydrochloride;
(±)-3n-hexyloxy-12-ethanesulfonyl-5,6,8aα,9,10,11,12,-
12aα,13,13aα-decahydro-8H-isoquino[2,1-
g][1,6]naphthyridine hydrochloride;
(±)-3-n-hexyloxy-12-ethanesulfonyl-
5,6,8aβ,9,10,11,12,12aβ,13,13-aα-decahydro-8H-
isoquino[2,1-g][1,6]naphthyridine hydrochloride;
(±)-2,3-diethoxy-12-ethanesulfonyl-5,6,8aα,9,10,11,12,-
12aα,13,13aα-decahydro-8H-isoquino[2,1-
g][1,6]naphthyridine hydrochloride;
(±)-2,3-diethoxy-12-ethanesulfonyl-5,6,8aβ,9,10,11,12,-
12aβ,13,13aα-decahydro-8H-isoquino[2,1-
g][1,6]naphthyridine hydrochloride;
(±)-3-chloro-12-ethanesulfonyl-5,6,8aα,9,10,11,12,-
12aα,13,13aα-decahydro-8H-isoquino[2,1-
g][1,6]naphthyridine hydrochloride;
(±)-3-chloro-12-ethanesulfonyl-5,6,8aβ,9,10,11,12,-
12aβ,13,13aα-decahydro-8H-isoquino[2,1-
g][1,6]naphthyridine hydrochloride;
(±)-3-methyl-12-(1-n-hexanesulfonyl)-
5,6,8aα,9,10,11,12,12aα,13,13aα-decahydro-8H-
isoquino[2,1-g][1,6]naphthyridine hydrochloride;
(±)-3-methoxy-12-(1n-hexanesulfonyl)-
5,6,8aβ,9,10,11,12,12aβ,13,13aα-decahydro-8H-
isoquino[2,1-g][1,6]naphthyridine hydrochloride;
(±)-3-methoxy-12-(1-n-hexanesulfonyl)-
5,6,8aα,9,10,11,12,12aα,13,13aα-decahydro-8H-
isoquino[2,1-g][1,6]naphthyridine hydrochloride;
(±)-2,3-dimethoxy-12-(1-n-hexanesulfonyl)-
5,6,8aβ,9,10,11,12,12aβ,13,13aα-decahydro-8H-
isoquino[2,1-g][1,6]naphthyridine hydrochloride;
(±)-2,3-dimethoxy-12-(1-n-hexanesulfonyl)-
5,6,8aα,9,10,11,12,12aα,13,13aα-decahydro-8H-
isoquino[2,1-g][1,6]naphthyridine hydrochloride;
(±)-3-chloro-12-(1-n-hexanesulfonyl)-
5,6,8aα,9,10,11,12,12aα,13,13aα-decahydro-8H-
isoquino[2,1-g][1,6]naphthyridine hydrochloride;
(±)-3-chloro-12-(1-n-hexanesulfonyl)-
5,6,8aβ,9,10,11,12,12aβ,13,13aα-decahydro-8H-
isoquino[2,1-g][1,6]naphthyridine hydrochloride;
(±)-3-methoxy-12-phenylsulfonyl-5,6,8aα,9,10,11,12,-
12aα,13,13aα-decahydro-8H-isoquino[2,1-
g][1,6]naphthyridine hydrochloride;
(±)-3-methoxy-12-phenylsulfonyl-5,6,8aβ,9,10,11,12,-
12aβ,13,13aα-decahydro-8H-isoquino[2,1-
g][1,6]naphthyridine hydrochloride;

(±)-3-methyl-12-(N,N-dimethylaminosulfonyl)-
  5,6,8aα,9,10,11,12,12aα,13,13aα-decahydro-8H-
  isoquino[2,1-g][1,6]naphthyridine hydrochloride;
(±)-3-methyl-12-(N,N-dimethylaminosulfonyl)-
  5,6,8aβ,9,10,11,12,12aβ,13,13aα-decahydro-8H-
  isoquino[2,1-g][1,6]naphthyridine hydrochloride;
(±)-3-methoxy-12-(N,N-dimethylaminosulfonyl)-
  5,6,8aα,9,10,11,12,12aα,13,13aα-decahydro-8H-
  isoquino[2,1-g][1,6]naphthyridine hydrochloride;
(±)-3-methoxy-12-(N,N-dimethylaminosulfonyl)-
  5,6,8aβ,9,10,11,12,12aβ,13,13aα-decahydro-8H-
  isoquino[2,1-g][1,6]naphthyridine hydrochloride;
(±)-2,3-dimethoxy-12-(N,N-dimethylaminosulfonyl)-
  5,6,8aα,9,10,11,12,12aα,13,13aα-decahydro-8H-
  isoquino[2,1-g][1,6]naphthyridine hydrochloride;
(±)-2,3-dimethoxy-12-(N,N-dimethylaminosulfonyl)-
  5,6,8aβ,9,10,11,12,12aβ,13,13aα-decahydro-8H-
  isoquino[2,1-g][1,6]naphthyridine hydrochloride;
(±)-12-(2-methoxypropanesulfonyl)-
  5,6,8aα,9,10,11,12,12aα,13,13aα-decahydro-8H-
  isoquino[2,1-g][1,6]naphthyridine hydrochloride;
(±)-12-(2-methoxypropanesulfonyl)-
  5,6,8aβ,9,10,11,12,12aβ,13,13aα-decahydro-8H-
  isoquino[2,1-g][1,6]naphthyridine hydrochloride;
(±)-12-(2-methoxyhexanesulfonyl)-5,6,8aα,9,10,11,12,-
  12aα,13,13aα-decahydro-8H-isoquino[2,1-
  g][1,6]naphthyridine hydrochloride;
(±)-12-(2-methoxyhexanesulfonyl)-5,6,8aβ,9,10,11,12,-
  12aβ,13,13aα-decahydro-8H-isoquino[2,1-
  g][1,6]naphthyridine hydrochloride;
(±)-2-methyl-12-(2-methoxymethanesulfonyl)-
  5,6,8aα,9,10,11,12,12aα,13,13aα-decahydro-8H-
  isoquino[2,1-g][1,6]naphthyridine hydrochloride;
(±)-2-methyl-12-(2-methoxymethanesulfonyl)-
  5,6,8aβ,9,10,11,12,12aβ,13,13aα-decahydro-8H-
  isoquino[2,1-g][1,6]naphthyridine hydrochloride;
(±)-2,3-methylenedioxy-12-(N,N-dimethylaminosul-
  fonyl)-5,6,8aα,9,10,11,12,12aα,13,13aα-decahydro-
  8H-isoquino[2,1-g][1,6]naphthyridine hydrochloride;
(±)-2,3-methylenedioxy-12-(N,N-dimethylaminosul-
  fonyl)-5,6,8aβ,9,10,11,12,12aβ,13,13aα-decahydro-
  8H-isoquino[2,1-g][1,6]naphthyridine hydrochloride;
(±)-3-n-hexyloxy-12-ethanesulfonyl-
  5,6,8aα,9,10,11,12,12aα,13,13aα-decahydro-8H-
  isoquino[2,1-g][1,6]naphthyridine hydrochloride;
(±)-3-n-hexyloxy-12-ethanesulfonyl-
  5,6,8aβ,9,10,11,12,12aβ,13,13aα-decahydro-8H-
  isoquino[2,1-g][1,6]naphthyridine hydrochloride;
(±)-2,3-diethoxy-12-ethanesulfonyl-5,6,8aα,9,10,11,12,-
  12aα,13,13aα-decahydro-8H-isoquino[2,1-
  g][1,6]naphthyridine hydrochloride;
(±)-2,3-diethoxy-12-ethanesulfonyl-5,6,8aβ,9,10,11,12,-
  12aβ,13,13aα-decahydro-8H-isoquino[2,1-
  g][1,6]naphthyridine hydrochloride;
(±)-3-chloro-12-ethanesulfonyl-5,6,8aα,9,10,11,12,-
  12aα,13,13aα-decahydro-8H-isoquino[2,1-
  g][1,6]naphthyridine hydrochloride; and
(±)-3-chloro-12-ethanesulfonyl-5,6,8aβ,9,10,11,12,-
  12aβ,13,13aα-decahydro-8H-isoquino[2,1-
  g][1,6]naphthyridine hydrochloride.

EXAMPLE 2

Alternative Preparation of
(±)-12-Methanesulfonyl-5,6,8aα,9,10,11,12,12aα,13,-
13aα-decahydro-8H-isoquino[2,1-g][1,6]naphthyridine
hydrochloride and Related Compounds of Formula (1)

A. A mixture of 1.14 g of (±)-12-methanesulfonyl-5,6,8aβ,9,10,11,12,12aβ,13,13aα-decahydro-8H-isoquino[2,1-g][1,6]naphthyridine (a compound of formula (2)) and 4.53 g of mercuric acetate in 20 ml of acetic acid and 2 ml of water was stirred at 105° C. for 1 hour. The mixture was filtered and hydrogen sulfide was bubbled through the filtrate for 5 minutes. The mixture was filtered again and the filtrate was concentrated under reduced pressure. Ethanol (50 ml) was added and the resulting solution was cooled to −20° C. and treated with 0.5 g of sodium borohydride. The solution was allowed to warm to room temperature and acidified with aqueous HCl. After washing with ethyl acetate, the aqueous layer was basified wth NH₄OH and extracted with ethyl acetate. The ethyl acetate was washed with brine, dried over anhydrous sodium sulfate and evaporated. Chromatography of the residue on silica gel, eluting with 1% methanol in methylene chloride, afforded the crystalline (±)-12-methanesulfonyl-5,6,8aα,9,10,11,12,12aα,13,13aα-decahydro-8H-isoquino[2,1-g][1,6]naphthyridine, m.p. XX°C. The hydrochloride salt was crystallized from ethanol: yield 0.4 g: m.p. 234°-235° C.

B. Similarly, replacing (±)-12-methanesulfonyl-5,6,8aβ,9,10,11,12,12aβ,13,13aα-decahydro-8H-isoquino[2,1-g][1,6]naphthyridine with other compounds of formula (2) and following the procedure in paragraph A above, the following compounds of formula (1) are prepared:

(±)-12-ethanesulfonyl-5,6,8aα,9,10,11,12,12aα,
  13,13aα-decahydro-[H-isoquino[2,1-g][1,6]naphthyridine;
(±)-3-methoxy-12-methanesulfonyl-5,6,8aα,9,10,11,12,-
  12aα,13,13aα-decahydro-8H-isoquino[2,1-
  g][1,6]naphthyridine;
(±)-3-methoxy-12-(2-methylpropanesulfonyl)-
  5,6,8aα,9,10,11,12,12aα,13,13aα-decahydro-8H-
  isoquino[2,1-g][1,6]naphthyridine;
(±)-2,3-dimethoxy-12-methanesulfonyl-
  5,6,8aα,9,10,11,12,12aα,13,13aα-decahydro-8H-
  isoquino[2,1-g][1,6]naphthyridine;
(±)-1,4-dimethoxy-12-methanesulfonyl-
  5,6,8aα,9,10,11,12,12aα,13,13aα-decahydro-8H-
  isoquino[2,1-g][1,6]naphthyridine;
(±)-2,3-dimethoxy-12-(2-methylpropanesulfonyl)-
  5,6,8aα,9,10,11,12,12aα,13,13aα-decahydro-8H-
  isoquino[2,1-g][1,6]naphthyridine;
(±)-2,3-methylenedioxy-12-methanesulfonyl-
  5,6,8aα,9,10,11,12,12aα,13,13aα-decahydro-8H-
  isoquino[2,1-g][1,6]naphthyridine;
(±)-2,3-methylenedioxy-12-(2-methylpropanesul-
  fonyl)-5,6,-8aα,9,10,11,12,12aα,13,13aα-decahydro-
  8H-isoquino[2,1-g][1,6]naphthyridine;
(±)-12-(1-butanesulfonyl)-5,6,8aα,9,10,11,12,12aα,13,-
  13aα-decahydro-8H-isoquino[2,1-g][1,6]naphthyridine;
(±)-12-(1-propanesulfonyl)-5,6,8aα,9,10,11,12,-
  12aα,13,13aα-decahydro-8H-isoquino[2,1-
  g][1,6]naphthyridine;

(±)-12-(2-methylpropanesulfonyl)-5,6,8aα,9,10,11,12,-12aα,13,13aα-decahydro-8H-isoquino[2,1-g][1,6]naphthyridine;
(±)-12-phenylsulfonyl-5,6,8aα,9,10,11,12,12aα,13,-13aα-decahydro-8H-isoquino[2,1-g][1,6]naphthyridine;
(±)-12-(4-methoxyphenylsulfonyl)-5,6,8aα,9,10,11,12,-12aα,13,13aα-decahydro-8H-isoquino[2,1-g][1,6]naphthyridine;
(±)-12-(4-chlorophenylsulfonyl)-5,6,8aα,9,10,11,12,-12aα,13,13aα-decahydro-8H-isoquino[2,1-g][1,6]naphthyridine;
(±)-12-(4-aminophenylsulfonyl)-5,6,8aα,9,10,11,12,-12aα,13,13aα-decahydro-8H-isoquino[2,1-g][1,6]naphthyridine;
(±)-12-(4-fluorophenylsulfonyl)-5,6,8aα,9,10,11,12,-12aα,13,13aα-decahydro-8H-isoquino[2,1-g][1,6]naphthyridine;
(±)-12-(2-methoxyethanesulfonyl)-5,6,8aα,9,10,11,12,-12aα,13,13aα-decahydro-8H-isoquino[2,1-g][1,6]naphthyridine;
(±)-12-(2-hydroxyethanesulfonyl)-5,6,8aα,9,10,11,12,-12aα,13,13aα-decahydro-8H-isoquino[2,1-g][1,6]naphthyridine; and
(±)-12-(N,N-dimethylaminosulfonyl)-5,6,8aα,9,10,11,12,12aα,13,13aα-decahydro-8H-isoquino[2,1-g][1,6]naphthyridine;
(±)-3-methyl-12-methanesulfonyl-5,6,8aα,9,10,11,12,-12aα,13,13aα-decahydro-8H-isoquino[2,1-g][1,6]naphthyridine hydrochloride;
(±)-2,3-dimethyl-12-methanesulfonyl-5,6,8aα,9,10,11,12,12aα,13,13aα-decahydro-8H-isoquino[2,1-g][1,6]naphthyridine hydrochloride;
(±)-2-n-hexyl-12-methanesulfonyl-5,6,8aα,9,10,11,12,-12aα,13,13aα-decahydro-8H-isoquino[2,1-g][1,6]naphthyridine hydrochloride;
(±)-2-methoxy-12-methanesulfonyl-5,6,8aα,9,10,11,12,-12aα,13,13aα-decahydro-8H-isoquino[2,1-g][1,6]naphthyridine hydrochloride;
(±)-3-ethoxy-12-methanesulfonyl-5,6,8aα,9,10,11,12,-12aα,13,13aα-decahydro-8H-isoquino[2,1-g][1,6]naphthyridine hydrochloride;
(±)-3-isobutoxy-12-methanesulfonyl-5,6,8aα,9,10,11,12,12aα,13,13aα-decahydro-8H-isoquino[2,1-g][1,6]naphthyridine hydrochloride;
(±)-3-n-hexyloxy-12-methanesulfonyl-5,6,8aα,9,10,11,12,12aα,13,13aα-decahydro-8H-isoquino[2,1-g][1,6]naphthyridine hydrochloride;
(±)-1,2-dimethoxy-12-methanesulfonyl-5,6,8aα,9,10,11,12,12aα,13,13aα-decahydro-8H-isoquino[2,1-g][1,6]naphthyridine hydrochloride;
(±)-2,3-diethoxy-12-methanesulfonyl-5,6,8aα,9,10,11,12,12aα,13,13aα-decahydro-8H-isoquino[2,1-g][1,6]naphthyridine hydrochloride;
(±)-2,3-di-n-butoxy-12-methanesulfonyl-5,6,8aα,9,10,11,12,12aα,13,13aα-decahydro-8H-isoquino[2,1-g][1,6]naphthyridine hydrochloride;
(±)-3,4-methylenedioxy-12-methanesulfonyl-5,6,8aα,9,10,11,12,12aα,13,13aα-decahydro-8H-isoquino[2,1-g][1,6]naphthyridine hydrochloride;
(±)-2-chloro-12-methanesulfonyl-5,6,8aα,9,10,11,12,-12aα,13,13aα-decahydro-8H-isoquino[2,1-g][1,6]naphthyridine hydrochloride;
(±)-3-chloro-12-methanesulfonyl-5,6,8aα,9,10,11,12,-12aα,13,13aα-decahydro-8H-isoquino[2,1-g][1,6]naphthyridine hydrochloride;
(±)-3-fluoro-12-methanesulfonyl-5,6,8aα,9,10,11,12,-12aα,13,13aα-decahydro-8H-isoquino[2,1-g][1,6]naphthyridine hydrochloride;
(±)-12-aminosulfonyl-5,6,8aα,9,10,11,12,12aα,13,13aα-decahydro-8H-isoquino[2,1-g][1,6]naphthyridine hydrochloride;
(±)-12-methylaminosulfonyl-5,6,8aα,9,10,11,12,-12aα,13,13aα-decahydro-8H-isoquino[2,1-g][1,6]naphthyridine hydrochloride;
(±)-12-diethylaminosulfonyl-5,6,8aα,9,10,11,12,-12aα,13,13aα-decahydro-8H-isoquino[2,1-g][1,6]naphthyridine hydrochloride;
(±)-12-di-n-hexylaminosulfonyl-5,6,8aα,9,10,11,12,-12aα,13,13aα-decahydro-8H-isoquino[2,1-g][1,6]naphthyridine hydrochloride;
(±)-12-(1-piperazinosulfonyl)-5,6,8aα,9,10,11,12,-12aα,13,13aα-decahydro-8H-isoquino[2,1-g][1,6]naphthyridine hydrochloride;
(±)-12-(b 1-morpholinosulfonyl)-5,6,8aα,9,10,11,12,-12aα,13,13aα-decahydro-8H-isoquino[2,1-g][1,6]naphthyridine hydrochloride;
(±)-12-(1-piperidinosulfonyl)-5,6,8aα,9,10,11,12,-12aα,13,13aα-decahydro-8H-isoquino[2,1-g][1,6]naphthyridine hydrochloride;
(±)-3-methyl-12-ethanesulfonyl-5,6,8aα,9,10,11,12,-12aα,13,13aα-decahydro-8H-isoquino[2,1-g][1,6]naphthyridine hydrochloride;
(±)-3-ethoxy-12-ethanesulfonyl-5,6,8aα,9,10,11,12,-12aα,13,13aα-decahydro-8H-isoquino[2,1-g][1,6]naphthyridine hydrochloride;
(±)-3-n-hexyloxy-12-ethanesulfonyl-5,6,8aα,9,10,11,12,12aα,13,13aα-decahydro-8H-isoquino[2,1-g][1,6]naphthyridine hydrochloride;
(±)-2,3-diethoxy-12-ethanesulfonyl-5,6,8aα,9,10,11,12,-12aα,13,13aα-decahydro-8H-isoquino[2,1-g][1,6]naphthyridine hydrochloride;
(±)-3-chloro-12-ethanesulfonyl-5,6,8aα,9,10,11,12,-12aα,13,13aα-decahydro-8H-isoquino[2,1-g][1,6]naphthyridine hydrochloride;
(±)-3-methyl-12-(1-n-hexanesulfonyl)-5,6,8aα,9,10,11,12,12aα,13,13aα-decahydro-8H-isoquino[2,1-g][1,6]naphthyridine hydrochloride;
(±)-3-methoxy-12-(1-n-hexanesulfonyl)-5,6,8aα,9,10,11,12,12aα,13,13aα-decahydro-8H-isoquino[2,1-g][1,6]naphthyridine hydrochloride;
(±)-2,3-dimethoxy-12-(1-n-hexanesulfonyl)-5,6,8aα,9,10,11,-12,12aα,13,13aα-decahydro-8H-isoquino[2,1-g][1,6]naphthyridine hydrochloride;
(±)-3-chloro-12-(1-n-hexanesulfonyl)-5,6,8aα,9,10,11,12,12aα,13,13aα-decahydro-8H-isoquino[2,1-g][1,6]naphthyridine hydrochloride;
(±)-3-methoxy-12-phenylsulfonyl-5,6,8aα,9,10,11,12,-12aα,13,13aα-decahydro-8H-isoquino[2,1-g][1,6]naphthyridine hydrochloride;
(±)-3-methyl-12-(N,N-dimethylaminosulfonyl)5,6,-,8aα,9,10,11,12,12aα,13,13aα-decahydro-8H-isoquino[2,1-g][1,6]naphthyridine hydrochloride;
(±)-3-methoxy-12-(N,N-dimethylaminosulfonyl)-5,6,8aα,9,10,11,12,12aα,13,13aα-decahydro-8H-isoquino[2,1-g][1,6]naphthyridine hydrochloride;
(±)-2,3-dimethoxy-12-(N,N-dimethylaminosulfonyl)-5,6,8aα,9,10,11,12,12aα,13,13aα-decahydro-8H-isoquino[2,1-g][1,6]naphthyridine hydrochloride;
(±)-2,3-methylenedioxy-12-(N,N-dimethylaminosulfonyl)-5,6,8aα,9,10,11,12,12aα,13,13aα-decahydro-8H-isoquino[2,1-g][1,6]naphthyridine hydrochloride;

(±)-3-n-hexyloxy-12-ethanesulfonyl-
5,6,8aα,9,10,11,12,12aα,13,13aα-decahydro-8H-
isoquino[2,1-g][1,6]naphthyridine hydrochloride;
(±)-2,3-diethoxy-12-ethanesulfonyl-5,6,8aα,9,10,11,12,-
12aα,13,13aα-decahydro-8H-isoquino[2,1-
g][1,6]naphthyridine hydrochloride; and
(±)-3-chloro-12-ethanesulfonyl-5,6,8aα,9,10,11,12,-
12aα,13,13aα-decahydro-8H-isoquino[2,1-
g][1,6]naphthyridine hydrochloride.

EXAMPLE 3

Preparation of
(±)-12-(2-Hydroxyethanesulfonyl-5,6,8aα,9,10,11,12,-
12aα,13,13aα-decahydro-8H-isoquino[2,1-g][1,6]naph-
thyridine hydrochloride A. A solution of 0.62 g of (±)-12-(2-methoxye-
thanesulfonyl)-5,6,8aα,9,10,11,12,12aα,13,13aα-decahy-
dro-8H-isoquino[2,1-g][1,6]naphthyridine in 25 ml of
methylene chloride was cooled to −60° C. and treated
with 2 ml of 1M BBr$_3$ in methylene chloride. The mixture was allowed to warm to room temperature and 50
ml of water was then added. The mixture was basified
with NH$_4$OH and extracted several times with methylene chloride. The methylene chloride extracts were
evaporated and the residue was purified by silica gel
chromatography to give the free base, which was
treated with ethanolic HCl-ether to give (±)-12-(2-
hydroxyethanesulfonyl)-5,6,8aα,9,10,11,12,12aα,13,-
13aα-decahydro-8H-isoquino[2,1-g][1,6]naphthyridine
hydrochloride, (0.45 g), m.p. 215°–216° C.

B. Similarly, replacing (±)-12-(2-methoxyethanesul-
fonyl)-5,6,8aα,9,10,11,12,12aα,13,13aα-decahydro-8H-
isoquino[2,1-g][1,6]naphthyridine with the appropriate
alkoxy-substituted compounds of formula (1) or (2) and
following the procedure in paragraph A above, the
following compounds of formula (1) and (2) are prepared:

(±)-12-(2-hydroxyethanesulfonyl)-5,6,8aβ,9,10,11,12,-
12aβ,13,13aα-decahydro-8H-isoquino[2,1-
g][1,6]naphthyridine hydrochloride
(±)-12-(2-hydroxypropanesulfonyl)-
5,6,8aα,9,10,11,12,12aα,13,13aα-decahydro-8H-
isoquino[2,1-g][1,6]naphthyridine hydrochloride;
(±)-12-(2-hydroxyhexanesulfonyl)-5,6,8aα,9,10,11,12,-
12aα,13,13aα-decahydro-8H-isoquino[2,1-
g][1,6]naphthyridine hydrochloride; and
(±)-2-methyl-12-(2-hydroxymethanesulfonyl)-
5,6,8aα,9,10,11,12,12aα,13,13aα-decahydro-8H-
isoquino[2,1-g][1,6]naphthyridine hydrochloride.

EXAMPLE 4

Preparation of
(±)-12-(4-Aminophenylsulfonyl)-5,6,8aα,9,10,11,12,-
12aα,13,13aα-decahydro-8H-isoquino[2,1-
g][1,6]naphthyridine hydrochloride A. A solution of 0.44 g of (±)-5,6,8aα,9,10,11,12,-
12aα,13,13aα-decahydro-8H-isoquino[2,1-g][1,6]naph-
thyridine (VII) in 10 ml of methylene chloride and 1 ml
of triethylamine was treated with 0.4 g of 4-nitroben-
zensulfonyl chloride and the resulting mixture was
stirred at room temperature for 1 hour. The mixture was
diluted with methylene chloride, washed with aqueous
NH$_4$OH, and evaporated. The residue was dissolved in
25 ml of ethanol and hydrogenated at 50 psi with 0.2 g
of 10% Pd-C for 6 hours. The catalyst was removed by
filtration and the filtrate was concentrated under reduced pressure to a residue which was dissolved in
ethanolic HCl. Addition of ether gave a precipitate
which was filtered off and dried under vacuum to give
(±)-12-(4-aminophenylsulfonyl)-5,6,8aα,9,10,11,12,-
12aα,13,13aα-decahydro-8H-isoquino[2,1-g][1,6]naph-
thyridine dihydrochloride: yield 0.27 g, m.p. 245°–247°
C.

B. Similarly, replacing (±)-5,6,8aα,9,10,11,12,-
12aα,13,13aα-decahydro-8H-isoquino[2,1-g][1,6]naph-
thyridine with the appropriate compounds of formula
(VII) or (VIII) and following the procedure in paragraph A above, the following compounds of formula (1)
and (2) are prepared:

(±)-12-(4-aminophenylsulfonyl)-5,6,8aβ,9,10,11,12,-
12aβ,13,13aα-decahydro-8H-isoquino[2,1-
g][1,6]naphthyridine hydrochloride;
(±)-3-methoxy-12-(4-aminophenylsulfonyl)-
5,6,8aα,9,10,11,12,12aα,13,13aα-decahydro-8H-
isoquino[2,1-g][1,6]naphthyridine hydrochloride;
(±)-3-hydroxy-12-(4-aminophenylsulfonyl)-
5,6,8aα,9,10,11,12,12aα,13,13aα-decahydro-8H-
isoquino[2,1-g][1,6]naphthyridine hydrochloride;
(±)-2,3-dimethoxy-12-(4-aminophenylsulfonyl)-
5,6,8aα,9,10,11,12,12aα,13,13aα-decahydro-8H-
isoquino[2,1-g][1,6]naphthyridine hydrochloride;
(±)-2,3-methylenedioxy-12-(4-aminophenylsul-
fonyl)5,6,8aα,9,10,11,12,12aα,13,13aα-decahydro-
8H-isoquino[2,1-g][1,6]naphthyridine hydrochloride;

EXAMPLE 5

Conversion of
(±)-12-methanesulfonyl-5,6,8aα,9,10,11,12,12aα,13,-
13aα-decahydro-8H-isoquino[2,1-g][1,6]naphthyridine
to its hydrochloride Excess 3% hydrogen chloride in methanol is added to
a solution of (±)-12-methanesulfonyl-
5,6,8aα,9,10,11,12,12aα,13,13aα-decahydro-8H-
isoquino[2,1-g][1,6]naphthyridine in 20 ml methanol.
Diethyl ether is added until precipitation is complete.
The product is filtered, washed with ether, air dried and
recrystallized from methanol/acetone to yield (±)-12-
methanesulfonyl-5,6,8aα,9,10,11,12,12aα,13,13aα-
decahydro-8H-isoquino[2,1-g][1,6]naphthyridine hydrochloride.

In a similar manner, all compounds of formula (1) and
(2) in free base form may be converted to the acid addition salts by treatment with the appropriate acid, for
example, hydrobromic acid, sulfuric acid, nitric acid,
phosphoric acid, acetic acid, propionic acid, glycolic
acid, pyruvic acid, oxalic acid, malonic acid, succinic
acid, malic acid, maleic acid, fumaric acid, tartaric acid,
citric acid, benzoic acid, cinnamic acid, mandelic acid,
methanesulfonic acid, ethanesulfonic acid, p-toluenesulfonic acid, and the like.

EXAMPLE 6

Conversion of a salt of
(±)-12-methanesulfonyl-5,6,8aα,9,10,11,12,12aα,13,-
13aα-decahydro-8H-isoquino[2,1-g][1,6]naphthyridine
to free base (±)-12-methanesulfonyl-5,6,8aα,9,10,11,12,12aα,13,-
13aα-decahydro-8H-isoquino[2,1-g][1,6]naphthyridine
hydrochloride suspended in 50 ml of ether is stirred
with excess dilute aqueous potassium carbonate solution
until the salt is completely dissolved. The organic layer
is then separated, washed twice with water, dried over
magnesium sulfate and evaporated to yield (±)-12-
methanesulfonyl-5,6,8aα,9,10,11,12,12aα,13,13aα- decahydro-8H-isoquino[2,1-g][1,6]naphthyridine, m.p. 176°–177° C.

In s similar manner the acid addition salts of all compounds of formula (1) and (2) may be converted to the corresponding compounds in free base form.

EXAMPLE 7

Direct interchange of acid addition salts of (±)-12-methanesulfonyl-5,6,8aα,9,10,11,12,12aα,13,-13aα-decahydro-8H-isoquino[2,1-g][1,6]naphthyridine.

(±)-12-Methanesulfonyl-5,6,8aα,9,10,11,12,12aα,13,-13aα-decahydro-8H-isoquino[2,1-g][1,6]naphthyridine acetate (1.0 g) is dissolved in 50 ml 5N aqueous hydrochloric acid, and the solution evaporated to dryness. The product is suspended in ethyl acetate and filtered, air dried and recrystallized from methanol/acetone to yield (±)-12-methanesulfonyl-5,6,8aα,9,10,11,12,12aα,-13,13aα-decahydro-8H-isoquino[2,1-g][1,6]naphthyridine hydrochloride.

In a similar manner, substituting for hydrochloric acid other acids, such as sulfuric acid, nitric acid, phosphoric acid and the like, other acid addition salts of all compounds of formula (1) and (2) are prepared.

In Examples 8 through 13 the active ingredient is (±)-12-methanesulfonyl-5,6,8aα,9,10,11,12,12aα,13,-13aα-decahydro-8H-isoquino[2,1-g][1,6]naphthyridine hydrochloride. Other compounds of formula (1) and (2) and the pharmaceutically acceptable salts thereof may be substituted therein.

EXAMPLE 8

Composition for Oral Administration

| The composition contains: | % wt./wt. |
| --- | --- |
| Active ingredient | 20% |
| Lactose | 80% |

The two ingredients are milled, mixed and dispensed into capsules containing 100 mg each; one capsule would approximate a total daily dosage.

EXAMPLE 9

Composition for Oral Administration

| The composition contains: | % wt./wt. |
| --- | --- |
| Active ingredient | 20.0% |
| Magnesium stearate | 0.9% |
| Starch | 8.6% |
| Lactose | 79.6% |
| PVP (polyvinylpyrrolidine) | 0.9% |

The above ingredients are combined and granulated using methanol as solvent. The formulation is then dried and formed into tablets (containing 20 mg of active compound) with an appropriate tableting machine.

EXAMPLE 10

Parenteral Formulation (IV)

| The composition contains: | % wt./wt. |
| --- | --- |
| Active ingredient | 0.25 g |
| Propylene glycol | 20. g |
| Polyethylene glycol 400 | 20. g |
| Polysorbate 80 | 1. g |// -continued
| The composition contains: | % wt./wt. |
| 0.9% Saline solution qs ad | 100 ml |

The active ingredient is dissolved in propylene glycol, polyethylene glycol 400 and polysorbate 80. A sufficient quantity of 0.9% saline solution is then added with stirring to provide 100 ml. of the I.V. solution which is filtered through a 0.2 micron membrane filter and packaged under sterile conditions.

EXAMPLE 11

Suppository Formulation

| The composition contains: | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 12

Composition for Topical Administration to the Eye

| The composition contains: | % wt/vol |
| --- | --- |
| Active ingredient | 0.10 |
| Benzalkonium chloride | 0.02 |
| EDTA | 0.01 |
| Phenylethanol | 0.25 |
| Boric acid | 1.62 |
| water qs and | to adjust pH 100 ml |

The first four ingredients are dissolved in less than the required total volume of water, and the pH adjusted to 7.4. The volume is then brought to 100 ml with additional water.

EXAMPLE 13

Assay for pre- and post-synaptic α-adrenoceptor blockade

Protocol:
(According to Caroon, J. M. et al., *J. Med. Chem.*, 1982, Vol. 25, 666.)

Contralateral, prostatic and epididymal portions of the rat isolated vas deferens were suspended in separate organ baths containing oxygenated Krebs-bicarbonate solution at 37° C. The test compound was added to the Krebs-bicarbonate solution bathing the epididymal and prostatic portions of vas deferens. The contralateral portions served as control tissues. All tissues were then allowed to equilibrate with the bathing solution for 30 minutes.

Pre-synaptic α-adrenoceptor blockade was determined using the prostatic portions of vas deferens. Following the equilibration period, dose-response curves for the inhibitory effect of xylazine on the contractile response of the vas deferens to single pulse nerve stimulation were obtained.

Post-synaptic α-adrenoceptor blockade was determined using the epididymal portions of rat vas deferens. Following the equilibration period, dose-response curves for the contractile effects of phenylephrine on the vas deferens were obtained.

EXAMPLE 14

Determination of Platelet Aggregation Inhibition

Protocol:

Blood platelets are collected in the standard manner, and incubated in an Aggregation Module Incubator-Cuvette in the presence of either the inhibitor to be tested, or without said inhibitor as a control. The aggregation of the platelets is observed after the addition of an inducer, and the samples are evaluated for the presence of a lag period and the slope of the aggregation curve, as well as the maximum height of the aggregation curve in comparison to the control. $IC_{50}$ values i.e. the concentration of inhibitor required for 50% inhibition can be calculated from the inflection point on the appropriate dose response curve.

EXAMPLE 15

Determination of Effect on Intraoccular Pressure

Protocol:

The compound to be tested is dissolved in saline, and applied topically to the eye. The intraoccular pressure is measured immediately before application, and at specified time intervals thereafter, by means of a probe which measures the force necessary to flatten a small area of corneal surface, according to the method described by Moses, R. A., *Tr. Am. Acad. Opth. and Otol.*, January-February 1962: 88-95.

I claim:

1. A compound of the formula (1) or (2):

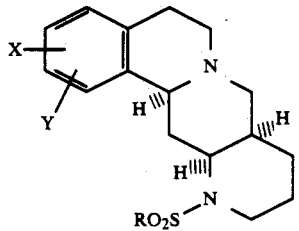

(1)

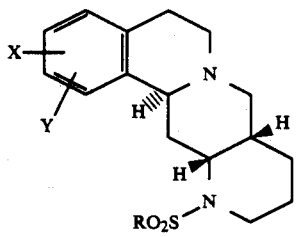

(2)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy; and
R is lower alkyl of one to six carbon atoms, phenyl optionally substituted by one or two substituents chosen from halo or nitro groups or lower alkyl or lower alkoxy groups of one to four carbon atoms, —$(CH_2)_m OR^1$ or —$NR^1 R^2$ wherein m is an integer of 1 to 6 and $R^1$ and $R^2$ are independently hydrogen or lower alkyl, or —$NR^1 R^2$ taken together is a heterocycle of the formula:

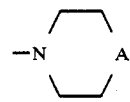

wherein A is —$CH_2$—, —$NR^1$— or oxygen; or a pharmaceutically acceptable salt thereof.

2. A compound of claim 1 which is a compound of formula (1), or a pharmaceutically acceptable salt thereof.

3. A compound of claim 2 in which X and Y are independently hydrogen or lower alkoxy having one to four carbon atoms, or X and Y taken together is methylenedioxy, or a pharmaceutically acceptable salt thereof.

4. A compound of claim 3 in which R is lower alkyl having one to six carbon atoms, or a pharmaceutically acceptable salt thereof.

5. A compound of claim 4 in which X and Y taken together is 2,3-methylenedioxy and R is methyl, namely (±)-2,3-methylenedioxy-12-methanesulfonyl-5,6,8a$\alpha$,9,10,11,12,12a$\alpha$,13,13a$\alpha$-decahydro-8H-isoquino[2,1-g][1,6]naphthyridine, or a pharmaceutically acceptable salt thereof.

6. A compound of claim 4 in which X and Y taken together is 2,3-methylenedioxy and R is 2-methylpropyl namely (±)-2,3-methylenedioxy-12-(2-methylpropanesulfonyl)-5,6,8a$\alpha$,9,10,11,12,12a$\alpha$,13,13a$\alpha$-decahydro8H-isoquino[2,1-g][1,6]naphthyridine, or a pharmaceutically acceptable salt thereof.

7. A compound of claim 4 in which X is 3-methoxy, Y is hydrogen and R is methyl, namely (±)-3-methoxy-12-methanesulfonyl-5,6,8a$\alpha$,9,10,11,12,12a$\alpha$,13,13a$\alpha$-decahydro-8H-isoquino[2,1-g][1,6]naphthyridine, or a pharmaceutically acceptable salt thereof.

8. A compound of claim 4 in which X is 3-methoxy, Y is hydrogen and R is 2-methylpropyl, namely (±)-3-methoxy-12-(2-methylpropanesulfonyl)-5,6,8a$\alpha$,9,10,11,12,12a$\alpha$,13,13a$\alpha$-decahydro-8H-isoquino[2,1-g][1,6]naphthyridine, or a pharmaceutically acceptable salt thereof.

9. A compound of claim 4 in which X is 2-methoxy, Y is 3-methoxy and R is methyl, namely (±)-2,3-dimethoxy-12-methanesulfonyl-5,6,8a$\alpha$,9,10,11,12,12a$\alpha$,13,-13a$\alpha$-decahydro-8H-isoquino[2,1-g][1,6]naphthyridine, or a pharmaceutically acceptable salt thereof.

10. A compound of claim 4 in which X and Y are both hydrogen and R is methyl, namely (±)-12-methanesulfonyl-5,6,8a$\alpha$,9,10,11,12,12a$\alpha$,13,13a$\alpha$-decahydro-8H-isoquino[2,1-g][1,6]naphthyridine, or a pharmaceutically acceptable salt thereof.

11. A compound of claim 4 in which X and Y are both hydrogen and R is 2-methylpropyl, namely (±)-12-(2-methylpropanesulfonyl)-5,6,8a$\alpha$,9,10,11,12,12a$\alpha$,13,-13a$\alpha$-decahydro-8H-isoquino[2,1-g][1,6]naphthyridine, or a pharmaceutically acceptable salt thereof.

12. A compound of claim 3 in which R is —$NR^1 R^2$, or a pharmaceutically acceptable salt thereof.

13. A compound of claim 12 in which $R^1$ and $R^2$ are independently hydrogen or lower alkyl of one to four carbon atoms, or a pharamceutically acceptable salt thereof.

14. A compound of claim 13 in which X and Y are both hydrogen and $R^1$ and $R^2$ are both methyl, namely (±)-12-(N,N-dimethylaminosulfonyl)-

5,6,8aα,9,10,11,12,12aα,13,13aα-decahydro-8H-isoquino[2,1-g][1,6]naphthyridine, or a pharmaceutically acceptable salt thereof.

15. A compound of claim 3 in which R is —(CH$_2$)$_m$OR$^1$, or a pharmaceutically acceptable salt thereof.

16. A compound of claim 15 in which m is 2 and R$^1$ is methyl, or a pharmaceutically acceptable salt thereof.

17. A compound of claim 16 in which X and Y are both hydrogen, namely (±)-12-(2-methoxyethanesulfonyl)-5,6,8aα,9,10,11,12,12aα,13,13aα-decahydro-8H-isoquino[2,1-g][1,6]naphthyridine, or a pharmaceutically acceptable salt thereof.

18. A compound of claim 16 in which X is 3-methoxy and Y is hydrogen, namely (±)-3-methoxy-12-(2-methoxyethanesulfonyl)-5,6,8aα,9,10,11,12,12aα,13,-13aα-decahydro-8H-isoquino[2,1-g][1,6]naphthyridine, or a pharmaceutically acceptable salt thereof.

19. A compound of claim 1 which is a compound of formula (2), or a pharmaceutically acceptable salt thereof.

20. A compound of claim 19 in which X and Y are independently hydrogen or lower alkoxy having one to four carbon atoms or X and Y taken together is methylenedioxy, or a pharmaceutically acceptable salt thereof.

21. A compound of claim 20 in which R is lower alkyl having one to four carbon atoms or —NR$^1$R$^2$, or a pharmaceutically acceptable salt thereof.

22. A composition suitable for administration to a mammal having a disease-state which is alleviated by treatment with an α$_2$-blocker, which composition comprises a pharmaceutically acceptable non-toxic carrier and a therapeutically effective amount of a compound of the formula

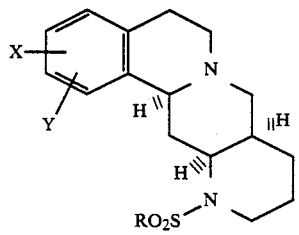

(1)

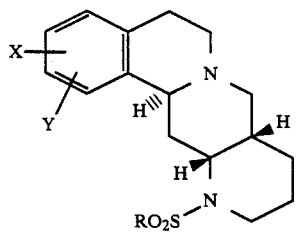

(2)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy; and R is lower alkyl of one to six carbon atoms, phenyl optionally substituted by one or two substituents chosen from halo or nitro groups or lower alkyl or lower alkoxy groups of one to four carbon atoms, —(CH$_2$)$_m$OR$^1$ or and R$^1$ and R$^2$ are independently hydrogen or lower alkyl, or —NR$^1$R$^2$ taken together is a heterocycle of the formula:

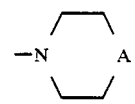

wherein A is —CH$_2$—, —NR$^1$— or oxygen;
or a pharmaceutically acceptable salt thereof, in admixture with one or more pharmaceutically acceptable carriers.

23. A method for treating a mammal having a disease-state which is alleviated by treatment with an α$_2$-blocker, which comprises administering a therapeutically effective amount of a compound of the formula

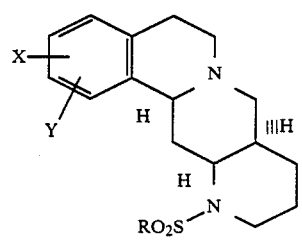

(1)

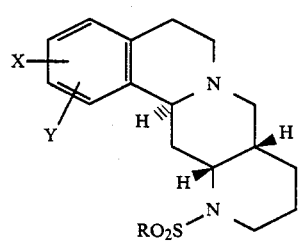

(2)

in which:
X and Y are independently hydrogen, hydroxy, lower alkyl of one to six carbon atoms, lower alkoxy of one to six carbon atoms or halo, or X and Y taken together is methylenedioxy or ethylene-1,2-dioxy; and R is lower alkyl of one to six carbon atoms, phenyl optionally substituted by one or two substituents chosen from halo or nitro groups or lower alkyl or lower alkoxy groups of one to four carbon atoms, —(CH$_2$)$_m$OR$^1$ or —NR$^1$R$^2$ wherein m is an integer of 1 to 6 and R$^1$ and R$^2$ are independently hydrogen or lower alkyl, or —NR$^1$R$^2$ taken together is a heterocycle of the formula:

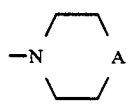

wherein A is —CH$_2$—, —NR$^1$— or oxygen;
or a pharmaceutically acceptable salt thereof.

24. The method of claim 19, wherein said disease-state is depression.

25. The method of claim 19, wherein said disease-state involves excessive platelet aggregation.

26. The method of claim 19, wherein said disease-state is diabetes.

27. The method of claim 19, wherein said disease-state is elevated intraoccular pressure.

28. The method of claim 19, wherein said disease-state is male impotence.

* * * * *